(12) United States Patent
Murphy et al.

(10) Patent No.: US 9,150,659 B2
(45) Date of Patent: Oct. 6, 2015

(54) ANTI-TACE ANTIBODY MOLECULES AND THEIR USES

(76) Inventors: Gillian Murphy, Cambridge (GB); Christopher Tape, London (GB); John McCafferty, Cambridge (GB)

(*) Notice: Subject to any disclaimer, the term of this patent is extended or adjusted under 35 U.S.C. 154(b) by 0 days.

(21) Appl. No.: 13/981,697

(22) PCT Filed: Jan. 30, 2012

(86) PCT No.: PCT/GB2012/000095
§ 371 (c)(1),
(2), (4) Date: Sep. 24, 2013

(87) PCT Pub. No.: WO2012/104581
PCT Pub. Date: Aug. 9, 2012

(65) Prior Publication Data
US 2014/0050738 A1 Feb. 20, 2014

Related U.S. Application Data

(60) Provisional application No. 61/438,354, filed on Feb. 1, 2011.

(51) Int. Cl.
| | |
|---|---|
| *A61K 39/00* | (2006.01) |
| *A61K 39/395* | (2006.01) |
| *C07K 16/00* | (2006.01) |
| *C07K 16/18* | (2006.01) |
| *C07K 16/40* | (2006.01) |
| *C07K 16/28* | (2006.01) |

(52) U.S. Cl.
CPC ............... *C07K 16/40* (2013.01); *C07K 16/00* (2013.01); *C07K 16/2896* (2013.01); *A61K 2039/505* (2013.01); *C07K 2317/30* (2013.01); *C07K 2317/34* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS 5,830,742 A * 11/1998 Black et al. .................. 435/226
2003/0175816 A1 9/2003 Black et al.

FOREIGN PATENT DOCUMENTS

WO 96/41624 12/1996
WO 2004/073734 A1 9/2004

OTHER PUBLICATIONS

Paul, Fundamental Immunology, 1993, Raven Press, New York, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
M. Moss et al., "Drug Insight: tumor necrosis factor-converting enzyme as a pharmaceutical target for rheumatoid arthritis", Nature Clinical Practice, 4(6): 300-309 (2008).
G. Murphy et al., "The ADAMs: signalling scissors in the tumour microenvironment", Nature Reviews: Cancer, 8(12): 929-941(2008).
D. Edwards et al., "The ADAM metalloproteinases", Mol. Aspects Med., 29(5): 258-289 (2008).
S. Willems et al., "Thiol isomerases negatively regulate the cellular shedding activity of ADAM17", Biochem. J., 428: 439-450 (2010).
C. Martin et al., "A simple vector system to improve performance and utilisation of recombinant antibodies", BMC Biotechnology, 6: 46 (2006).
M. Milla et al., Specific Sequence Elements Are Required for the Expression of Functional Tumor Necrosis Factoralpha-converting Enzyme (TACE), J. Biol. Chem., 274(43): 30563-30570 (1999).
Lendeckel, Uwe et al., "Increased expression of ADAM family members in human breast cancer and breast cancer cell lines", 131: 41-48 (2005).
Tape, Christopher J., "Cross-domain inhibition of TACE ectodomain", 108(14): 5578-5583 (2011).
International Search Report and Written Opinion, dated May 25, 2012, in corresponding International Application No. PCT/GB2012/000095.

* cited by examiner

*Primary Examiner* — Elizabeth C Kemmerer
(74) *Attorney, Agent, or Firm* — Patrick J. Hagan; Dann, Dorfman, Herrell and Skillman, P.C.

(57) ABSTRACT

Anti-TACE (ADAM17) antibodies are disclosed that for the first time in the art are capable of binding to TACE, of acting as antagonists of one or more its biological activities, in particular by binding to TACE in a cross domain binding mode in which residues in both the catalytic domain and in the cysteine rich/disintegrin domains (Dis-Cys) are involved in antibody binding to TACE, helping to improve the specificity of the antibody binding and/or helping to improve inhibition of TACE biological activity. The therapeutic uses of the antibodies, in particular for the treatment of cancer are disclosed.

8 Claims, 24 Drawing Sheets

A

Catalytic Domain
*Similar Between MPs*

Catalytic Site

Dis-Cys Domain
*Variable Between MPs*

TACE Ectodomain

B

(i) Primary Selections
Library: Naive scFv
Antigen: Catalytic Site Blocked

CT1746

(ii) Primary Screening
Identified ScFv D1
$V_H$-Paratope; Dis-Cys Epitope

D1-$V_L$
D1-$V_H$
*TACE Specific*

(iii) Secondary Selections
Library: D1-$V_H$-Neo-$V_L$
Antigen: Catalytic Site Exposed Neo-$V_L$s
D1-$V_H$
*TACE Specific*

(iv) Secondary Screening
Identified ScFv D1(A12)
Cross-Domain Epitope

A12-$V_L$
*Catalytic Blocked*
D1-$V_H$
*TACE Specific*

*Fig. 1*

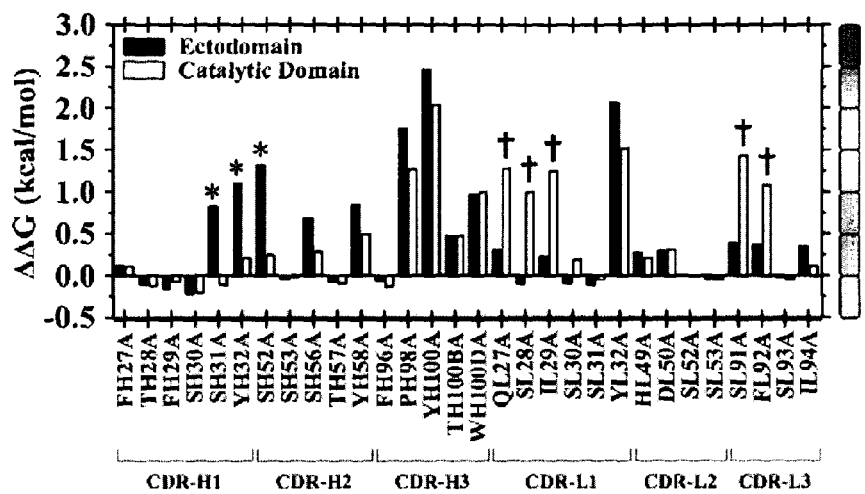
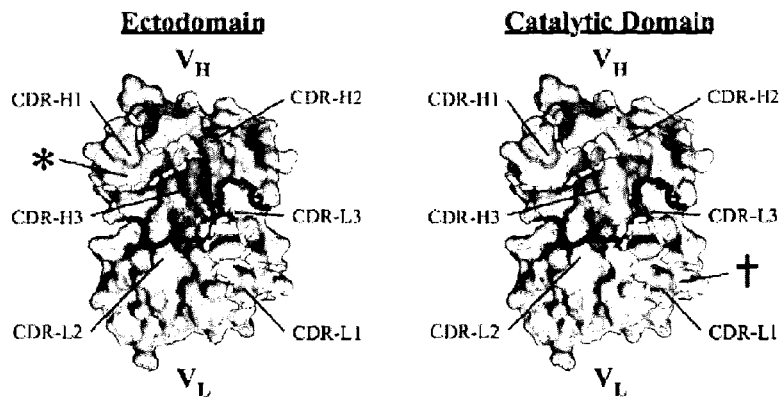
Fig. 4A

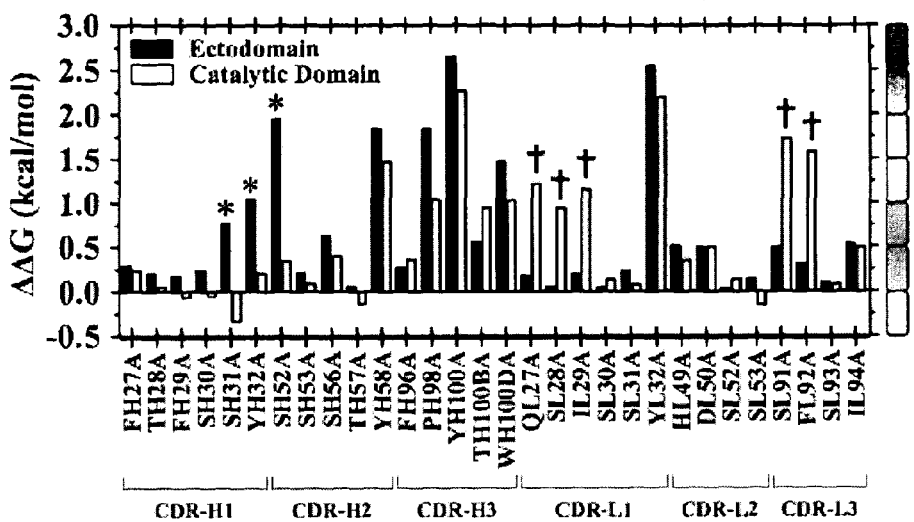
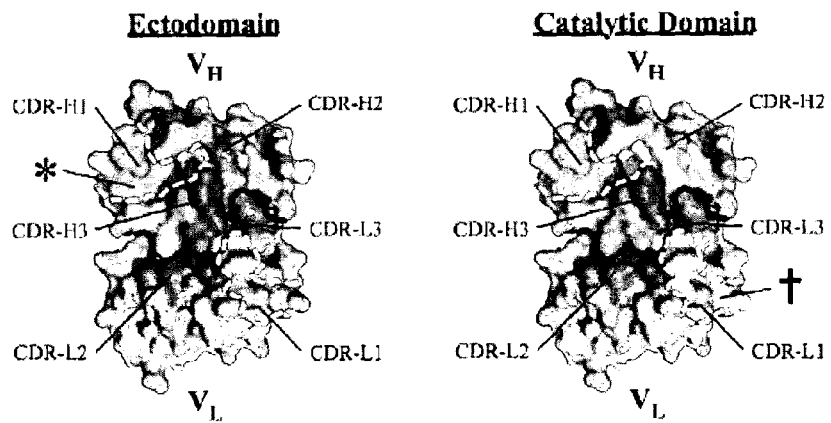
Fig. 4B

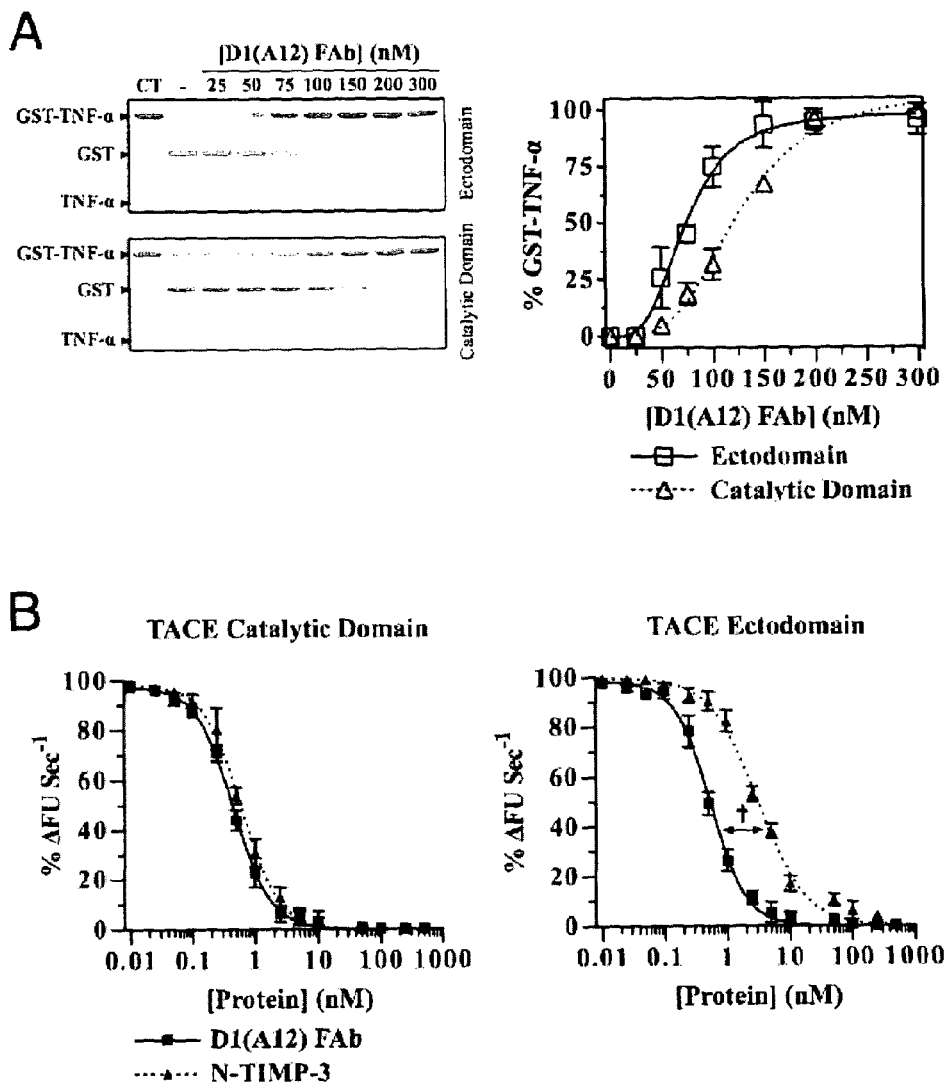
Fig. 5A, B

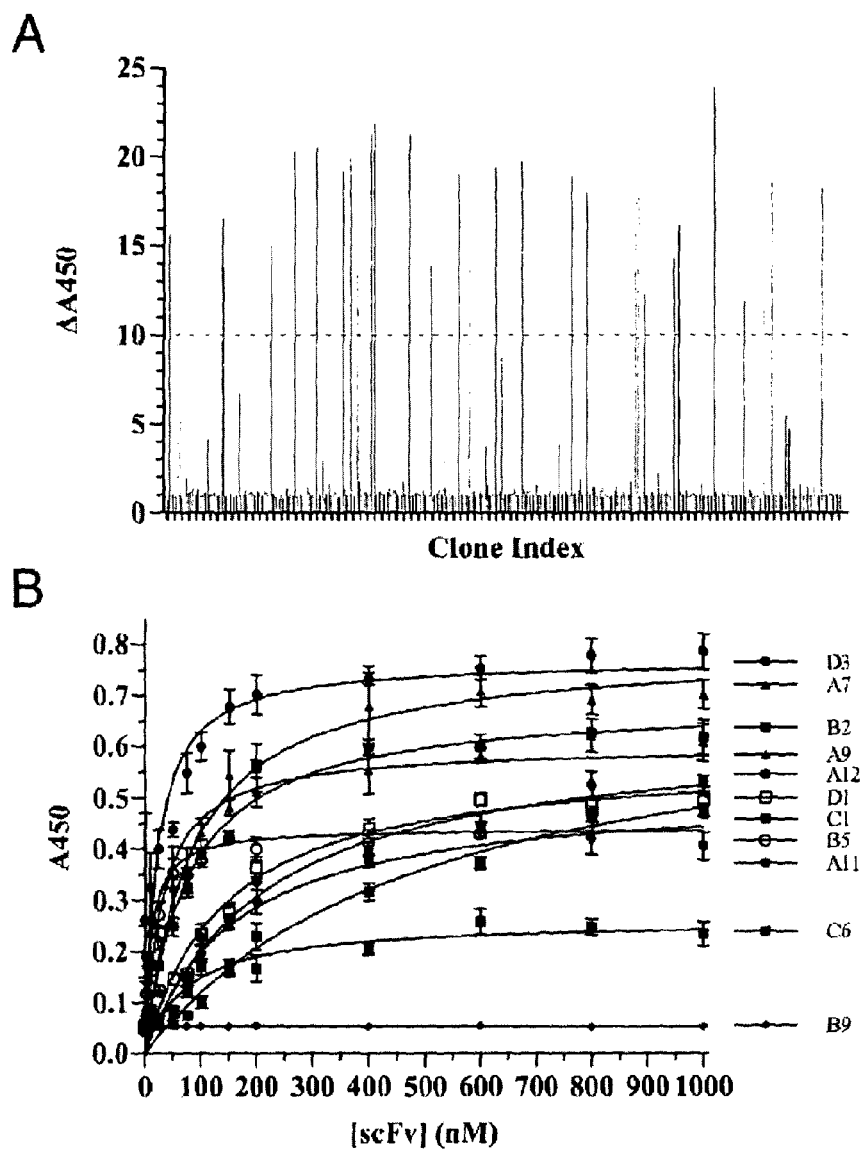
Fig. 7A, B

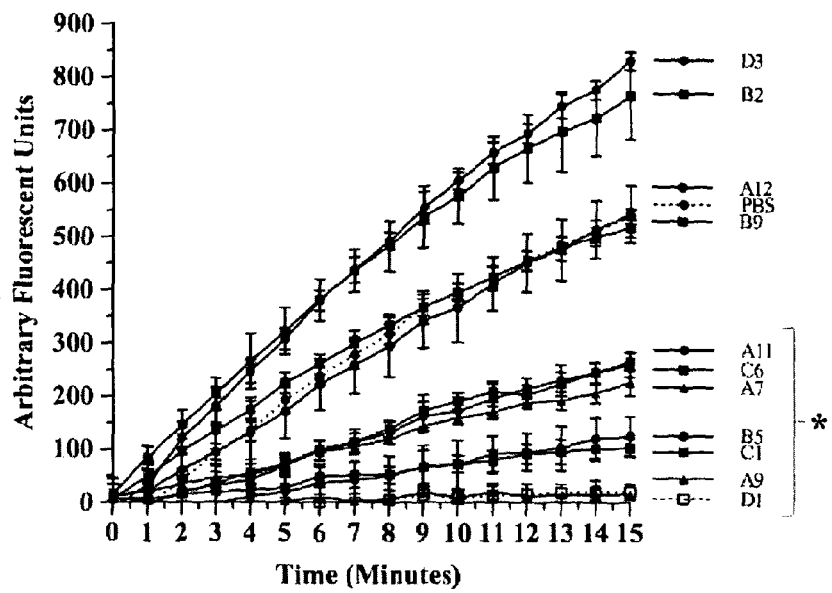
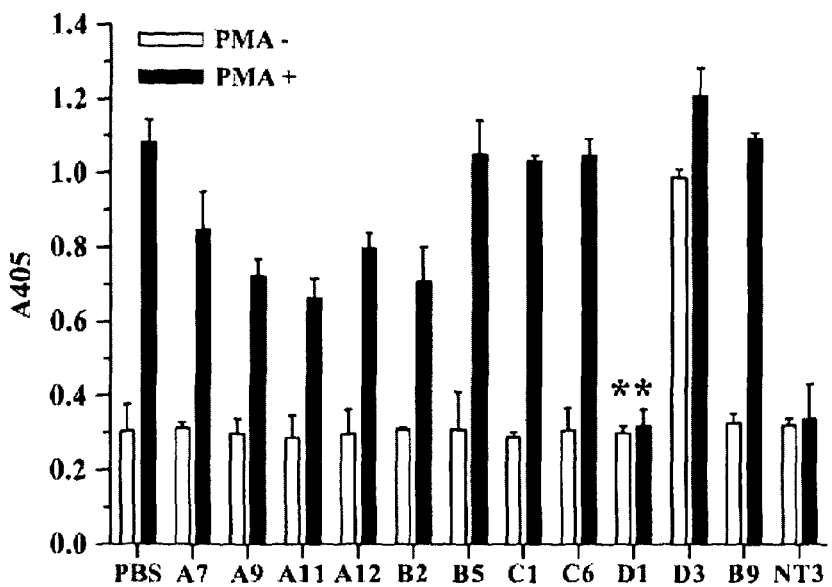
Fig. 7C, D

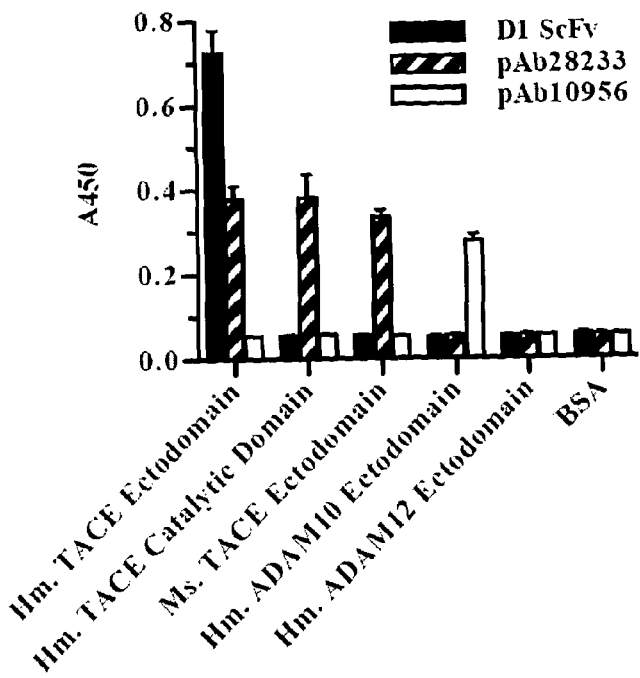
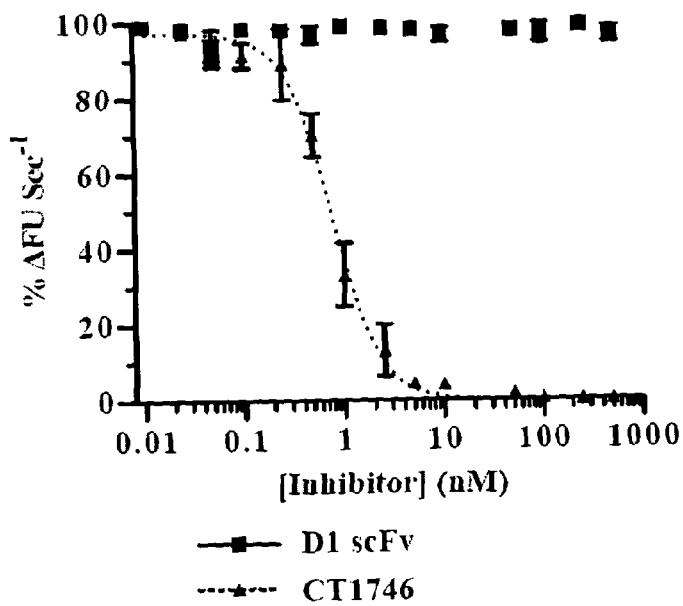
Fig. 8

A
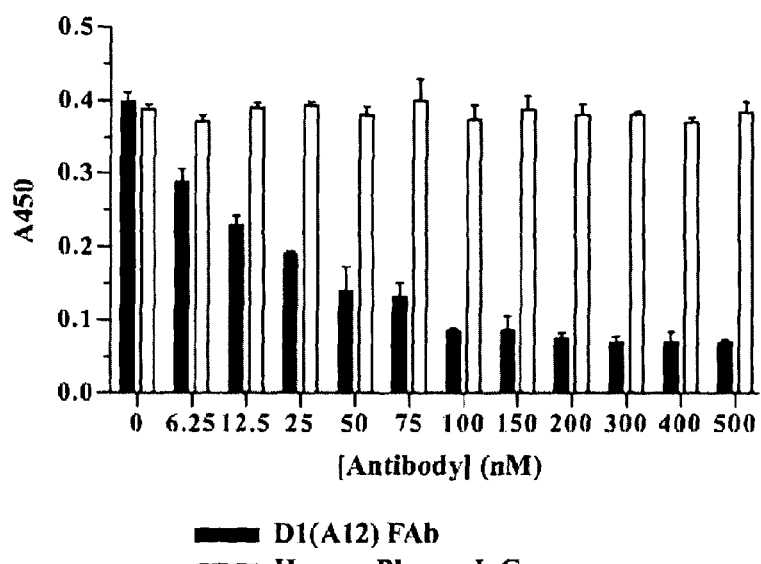
B
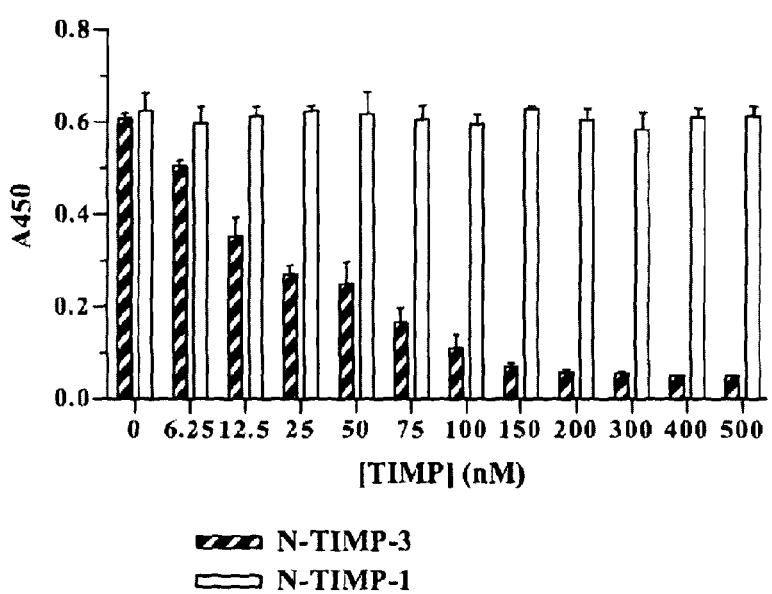
Fig. 9

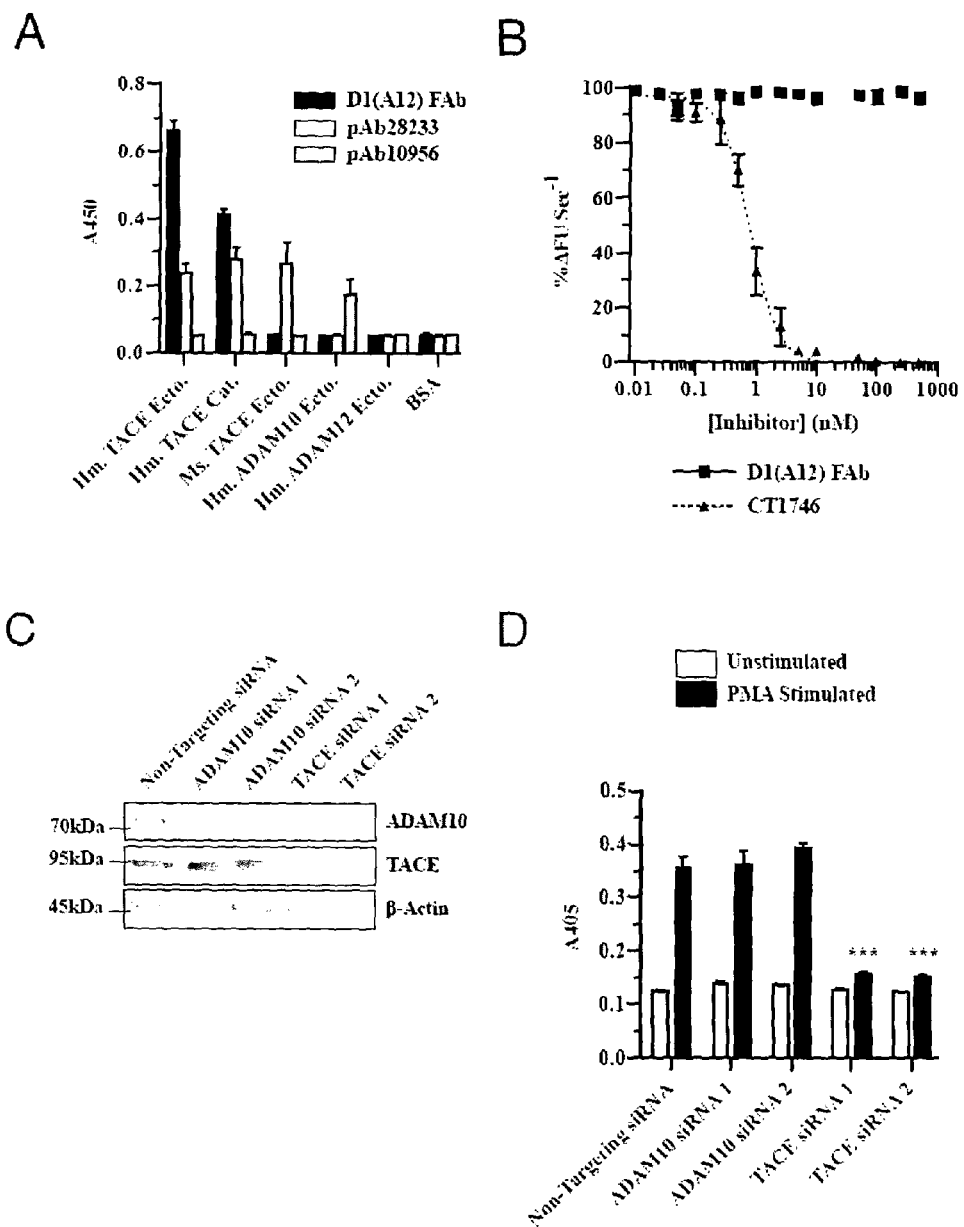
Fig. 11A-D

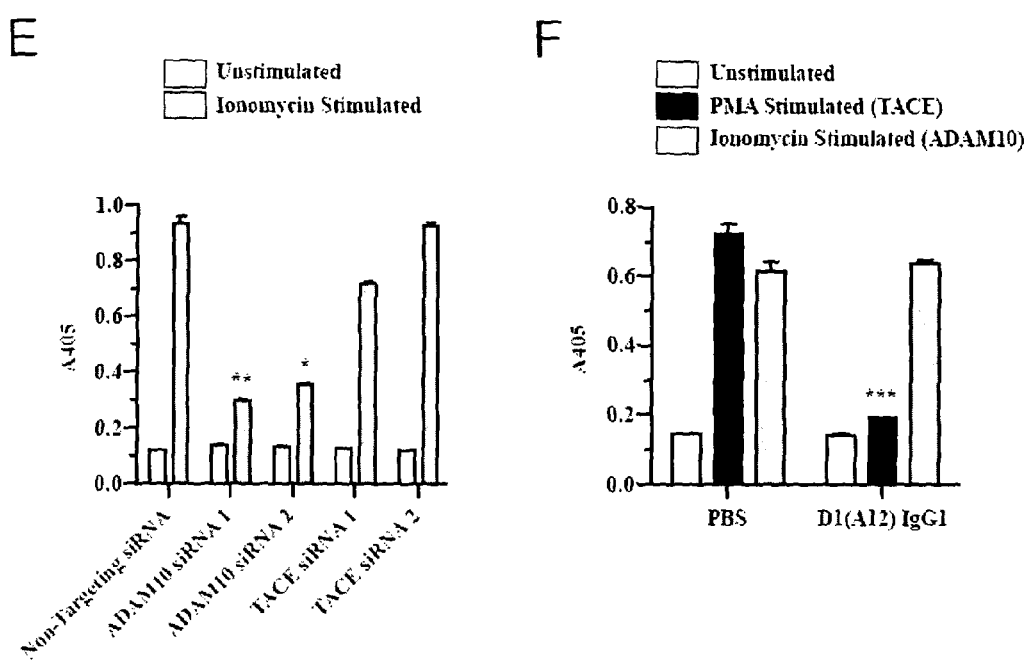
Fig. 11E, F

```
                         SEQUENCE LISTING

<160> NUMBER OF SEQ ID NOS: 20

<210> SEQ ID NO 1
<211> LENGTH: 14
<212> TYPE: PRT
<213> ORGANISM: Homo sapiens

<400> SEQUENCE: 1

Cys Ala Ala Ser Gly Phe Thr Phe Ser Ser Tyr Ala Met Ser
1               5                   10

<210> SEQ ID NO 2
<211> LENGTH: 17
<212> TYPE: PRT
<213> ORGANISM: Homo sapiens

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 16
<212> TYPE: PRT
<213> ORGANISM: Homo sapiens

<400> SEQUENCE: 3

Cys Val Lys Asp Phe Gly Pro Gly Tyr Gly Thr Gly Trp Phe Asp Tyr
1               5                   10                  15

<210> SEQ ID NO 4
<211> LENGTH: 12
<212> TYPE: PRT
<213> ORGANISM: Homo sapiens

<400> SEQUENCE: 4

Cys Arg Ala Ser Gln Ser Ile Ser Ser Tyr Leu Asn
1               5                   10
```

<210> SEQ ID NO 5
<211> LENGTH: 11
<212> TYPE: PRT
<213> ORGANISM: Homo sapiens

<400> SEQUENCE: 5

Ile His Asp Ala Ser Ser Leu Gln Ser Gly Val
1               5                   10

<210> SEQ ID NO 6
<211> LENGTH: 13
<212> TYPE: PRT
<213> ORGANISM: Homo sapiens

<400> SEQUENCE: 6

Cys Gln Gln Ser Phe Ser Ile Pro Leu Thr Phe Gly Gly
1               5                   10

<210> SEQ ID NO 7
<211> LENGTH: 122
<212> TYPE: PRT
<213> ORGANISM: Homo sapiens

<400> SEQUENCE: 7

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Thr Ser Leu Arg Ala Asp Asp Thr Ala Phe Tyr Tyr Cys
            85                  90                  95

Val Lys Asp Phe Gly Pro Gly Tyr Gly Thr Gly Trp Phe Asp Tyr Trp
            100                 105                 110

Gly Pro Gly Thr Leu Val Thr Val Ser Ala
            115                 120

<210> SEQ ID NO 8
<211> LENGTH: 366
<212> TYPE: DNA
<213> ORGANISM: Homo sapiens

<400> SEQUENCE: 8
gaagtgcagc tggtggagtc tgggggaggc ttggtacggc ctgggggtc cctgagactc        60 tcctgtgcag cctctggatt cacctttagc agctatgcca tgagctgggt ccgccaggct      120
ccagggaagg ggctggagtg gtctcagct attagtggta gtggtggtag cacatactac       180
gcagactccg tgaagggccg gttcaccatc tccagagaca acaccaagaa ctccctgtat      240
ctgcaaatga cgagtctgag agctgacgac acggcctttt attactgtgt aaaagatttc     300
ggacccggtt atggcactgg ctggtttgac tactggggcc cgggaaccct ggtcaccgtc      360
tccgca                                                                 366

<210> SEQ ID NO 9
<211> LENGTH: 109
<212> TYPE: PRT

<213> ORGANISM: Homo sapiens

<400> SEQUENCE: 9

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile His Asp Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Phe Ser Ile Pro
                85                  90                  95

Leu Thr Phe Gly Gly Gly Thr Lys Met Asp Ile Lys Arg
            100                 105

<210> SEQ ID NO 10
<211> LENGTH: 327
<212> TYPE: DNA
<213> ORGANISM: Homo sapiens

<400> SEQUENCE: 10
agcgacatcc agatgaccca gtctccatcc tccctgtctg catctgtagg agacagagtc      60
accatcactt gccgggcaag tcagagcatt agcagctatt taaattggta tcagcagaaa    120
ccagggaaag cccctaagct cctgatccat gatgcatcca gtttgcaaag tggggtccca    180
tcaaggttca gtggcagtgg atctgggaca gatttcactc tcaccatcag cagtctgcaa    240
cctgaagatt ttgcaactta ctactgtcaa cagagtttca gtattcccct cactttcggc    300
ggagggacca aatggatat caaacgt                                         327

<210> SEQ ID NO 11
<211> LENGTH: 225
<212> TYPE: PRT
<213> ORGANISM: Homo sapiens

<400> SEQUENCE: 11

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Thr Lys Asn Ser Leu Tyr
65                  70                  75                  80

Leu Gln Met Thr Ser Leu Arg Ala Asp Asp Thr Ala Phe Tyr Tyr Cys
                85                  90                  95

Val Lys Asp Phe Gly Pro Gly Tyr Gly Thr Gly Trp Phe Asp Tyr Trp
            100                 105                 110

Gly Pro Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 12
<211> LENGTH: 215
<212> TYPE: PRT
<213> ORGANISM: Homo sapiens

<400> SEQUENCE: 12

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile His Asp Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Phe Ser Ile Pro
                85                  90                  95

Leu Thr Phe Gly Gly Gly Thr Lys Met Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 13
<211> LENGTH: 675
<212> TYPE: DNA
<213> ORGANISM: Homo sapiens

<400> SEQUENCE: 13
gaagtgcagc tggtggagtc tgggggaggc ttggtacggc ctggggggtc cctgagactc    60

```
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca acaccaagaa ctccctgtat    240
ctgcaaatga cgagtctgag agctgacgac acggccttt  attactgtgt aaaagatttc    300
ggacccggtt atggcactgg ctggtttgac tactggggcc cgggaaccct ggtcaccgtc    360
tccgcagcct ccaccaaggg cccatcggtc ttccccctgg cacccctc  caagagcacc    420 tctggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgt                                                    675
```

<210> SEQ ID NO 14
<211> LENGTH: 645
<212> TYPE: DNA
<213> ORGANISM: Homo sapiens

<400> SEQUENCE: 14

```
agcgacatcc agatgaccca gtctccatcc tccctgtctg catctgtagg agacagagtc     60
accatcactt gccgggcaag tcagagcatt agcagctatt taaattggta tcagcagaaa    120
ccagggaaag cccctaagct cctgatccat gatgcatcca gtttgcaaag tggggtccca    180
tcaaggttca gtggcagtgg atctgggaca gatttcactc tcaccatcag cagtctgcaa    240
cctgaagatt ttgcaactta ctactgtcaa cagagtttca gtattcccct cactttcggc    300
ggagggacca aaatggatat caaacgtact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac  aaagtctacg cctgcgaagt cacccatcag    600
ggcctgagct cgcccgtcac aaagagcttc aacaggggag agtgt                   645
```

<210> SEQ ID NO 15
<211> LENGTH: 471
<212> TYPE: PRT
<213> ORGANISM: Homo sapiens

<400> SEQUENCE: 15

```
Met Asp Trp Thr Trp Arg Val Phe Cys Leu Leu Ala Val Ala Pro Gly
1               5                   10                  15

Ala His Ser Glu Val Gln Leu Val Glu Ser Gly Gly Gly Leu Val Arg
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Thr Lys Asn
                85                  90                  95

Ser Leu Tyr Leu Gln Met Thr Ser Leu Arg Ala Asp Asp Thr Ala Phe
```

```
              100                 105                 110
Tyr Tyr Cys Val Lys Asp Phe Gly Pro Gly Tyr Gly Thr Gly Trp Phe
            115                 120                 125

Asp Tyr Trp Gly Pro Gly Thr Leu Val Thr Val Ser Ala Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 16
<211> LENGTH: 235
<212> TYPE: PRT
<213> ORGANISM: Homo sapiens

<400> SEQUENCE: 16
```

Met Ala Trp Thr Pro Leu Trp Leu Thr Leu Phe Thr Leu Cys Ile Gly
1               5                   10                  15

Ser Val Val Ser Ser Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Ile Ser Ser Tyr Leu Asn Trp Tyr Gln Gln Lys Pro Gly Lys Ala
50                  55                  60

Pro Lys Leu Leu Ile His Asp Ala Ser Ser Leu Gln Ser Gly Val Pro
65                  70                  75                  80

Ser Arg Phe Ser Gly Ser Gly Ser Gly Thr Asp Phe Thr Leu Thr Ile
            85                  90                  95

Ser Ser Leu Gln Pro Glu Asp Phe Ala Thr Tyr Tyr Cys Gln Gln Ser
        100                 105                 110

Phe Ser Ile Pro Leu Thr Phe Gly Gly Gly Thr Lys Met Asp Ile Lys
    115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
        180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 17
<211> LENGTH: 1413
<212> TYPE: DNA
<213> ORGANISM: Homo sapiens

<400> SEQUENCE: 17
atggactgga cctggagggt cttctgcttg ctggctgtag caccaggtgc ccactccgaa      60
gtgcagctgg tggagtctgg gggaggcttg gtacggcctg gggggtccct gagactctcc     120
tgtgcagcct ctggattcac ctttagcagc tatgccatga gctgggtccg ccaggctcca     180
gggaaggggc tggagtgggt ctcagctatt agtggtagtg gtggtagcac atactacgca     240
gactccgtga agggccggtt caccatctcc agagacaaca ccaagaactc cctgtatctg     300
caaatgacga gtctgagagc tgacgacacg gccttttatt actgtgtaaa agatttcgga     360
cccggttatg gcactggctg gtttgactac tgggcccggg aaccctggt caccgtctcc      420 gcagcctcca ccaagggccc atcggtcttc cccctggcac cctcctccaa gagcacctct     480
gggggcacag cggccctggg ctgcctggtc aaggactact cccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780

```
ggaccgtcag tcttcctctt cccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagccc cgagaaccag caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tatagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaa                                 1413

<210> SEQ ID NO 18
<211> LENGTH: 705
<212> TYPE: DNA
<213> ORGANISM: Homo sapiens

<400> SEQUENCE: 18
atggcctgga cccctctctg gctcactctc ttcactcttt gcataggttc tgtggtttct      60
agcgacatcc agatgaccca gtctccatcc tccctgtctg catctgtagg agacagagtc     120
accatcactt gccgggcaag tcagagcatt agcagctatt taaattggta tcagcagaag     180
ccagggaaag cccctaagct cctgatccat gatgcatcca gtttgcaaag tggggtccca     240
tcaaggttca gtggcagtgg atctgggaca gatttcactc tcaccatcag cagtctgcaa     300
cctgaagatt ttgcaactta ctactgtcaa cagagtttca gtattcccct cactttcggc     360
ggagggacca aaatggatat caaacgtact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgt                    705

<210> SEQ ID NO 19
<211> LENGTH: 824
<212> TYPE: PRT
<213> ORGANISM: Homo sapiens

<400> SEQUENCE: 19

Met Arg Gln Ser Leu Leu Phe Leu Thr Ser Val Pro Phe Val Leu
1               5                   10                  15

Ala Pro Arg Pro Pro Asp Asp Pro Gly Phe Gly Pro His Gln Arg Leu
                20                  25                  30

Glu Lys Leu Asp Ser Leu Leu Ser Asp Tyr Asp Ile Leu Ser Leu Ser
            35                  40                  45

Asn Ile Gln Gln His Ser Val Arg Lys Arg Asp Leu Gln Thr Ser Thr
        50                  55                  60

His Val Glu Thr Leu Leu Thr Phe Ser Ala Leu Lys Arg His Phe Lys
65                  70                  75                  80

Leu Tyr Leu Thr Ser Ser Thr Glu Arg Phe Ser Gln Asn Phe Lys Val
                85                  90                  95
```

```
Val Val Val Asp Gly Lys Asn Glu Ser Glu Tyr Thr Val Lys Trp Gln
            100                 105                 110

Asp Phe Phe Thr Gly His Val Val Gly Glu Pro Asp Ser Arg Val Leu
        115                 120                 125

Ala His Ile Arg Asp Asp Val Ile Ile Arg Ile Asn Thr Asp Gly
    130                 135                 140

Ala Glu Tyr Asn Ile Glu Pro Leu Trp Arg Phe Val Asn Asp Thr Lys
145                 150                 155                 160

Asp Lys Arg Met Leu Val Tyr Lys Ser Glu Asp Ile Lys Asn Val Ser
                165                 170                 175

Arg Leu Gln Ser Pro Lys Val Cys Gly Tyr Leu Lys Val Asp Asn Glu
            180                 185                 190

Glu Leu Leu Pro Lys Gly Leu Val Asp Arg Glu Pro Pro Glu Glu Leu
        195                 200                 205

Val His Arg Val Lys Arg Arg Ala Asp Pro Asp Pro Met Lys Asn Thr
    210                 215                 220

Cys Lys Leu Leu Val Val Ala Asp His Arg Phe Tyr Arg Tyr Met Gly
225                 230                 235                 240

Arg Gly Glu Glu Ser Thr Thr Thr Asn Tyr Leu Ile Glu Leu Ile Asp
                245                 250                 255

Arg Val Asp Asp Ile Tyr Arg Asn Thr Ser Trp Asp Asn Ala Gly Phe
            260                 265                 270

Lys Gly Tyr Gly Ile Gln Ile Glu Gln Ile Arg Ile Leu Lys Ser Pro
        275                 280                 285

Gln Glu Val Lys Pro Gly Glu Lys His Tyr Asn Met Ala Lys Ser Tyr
    290                 295                 300

Pro Asn Glu Glu Lys Asp Ala Trp Asp Val Lys Met Leu Leu Glu Gln
305                 310                 315                 320

Phe Ser Phe Asp Ile Ala Glu Glu Ala Ser Lys Val Cys Leu Ala His
                325                 330                 335

Leu Phe Thr Tyr Gln Asp Phe Asp Met Gly Thr Leu Gly Leu Ala Tyr
            340                 345                 350

Val Gly Ser Pro Arg Ala Asn Ser His Gly Gly Val Cys Pro Lys Ala
        355                 360                 365

Tyr Tyr Ser Pro Val Gly Lys Lys Asn Ile Tyr Leu Asn Ser Gly Leu
    370                 375                 380

Thr Ser Thr Lys Asn Tyr Gly Lys Thr Ile Leu Thr Lys Glu Ala Asp
385                 390                 395                 400

Leu Val Thr Thr His Glu Leu Gly His Asn Phe Gly Ala Glu His Asp
                405                 410                 415

Pro Asp Gly Leu Ala Glu Cys Ala Pro Asn Glu Asp Gln Gly Gly Lys
            420                 425                 430

Tyr Val Met Tyr Pro Ile Ala Val Ser Gly Asp His Glu Asn Asn Lys
        435                 440                 445

Met Phe Ser Asn Cys Ser Lys Gln Ser Ile Tyr Lys Thr Ile Glu Ser
    450                 455                 460

Lys Ala Gln Glu Cys Phe Gln Glu Arg Ser Asn Lys Val Cys Gly Asn
465                 470                 475                 480

Ser Arg Val Asp Glu Gly Glu Glu Cys Asp Pro Gly Ile Met Tyr Leu
                485                 490                 495
```

```
Asn Asn Asp Thr Cys Cys Asn Ser Asp Cys Thr Leu Lys Glu Gly Val
            500                 505                 510

Gln Cys Ser Asp Arg Asn Ser Pro Cys Cys Lys Asn Cys Gln Phe Glu
            515                 520                 525

Thr Ala Gln Lys Lys Cys Gln Glu Ala Ile Asn Ala Thr Cys Lys Gly
            530                 535                 540

Val Ser Tyr Cys Thr Gly Asn Ser Ser Glu Cys Pro Pro Gly Asn
545                 550                 555                 560

Ala Glu Asp Asp Thr Val Cys Leu Asp Leu Gly Lys Cys Lys Asp Gly
            565                 570                 575

Lys Cys Ile Pro Phe Cys Glu Arg Glu Gln Gln Leu Glu Ser Cys Ala
            580                 585                 590

Cys Asn Glu Thr Asp Asn Ser Cys Lys Val Cys Arg Asp Leu Ser
            595                 600                 605

Gly Arg Cys Val Pro Tyr Val Asp Ala Glu Gln Lys Asn Leu Phe Leu
            610                 615                 620

Arg Lys Gly Lys Pro Cys Thr Val Gly Phe Cys Asp Met Asn Gly Lys
625                 630                 635                 640

Cys Glu Lys Arg Val Gln Asp Val Ile Glu Arg Phe Trp Asp Phe Ile
            645                 650                 655

Asp Gln Leu Ser Ile Asn Thr Phe Gly Lys Phe Leu Ala Asp Asn Ile
            660                 665                 670

Val Gly Ser Val Leu Val Phe Ser Leu Ile Phe Trp Ile Pro Phe Ser
            675                 680                 685

Ile Leu Val His Cys Val Asp Lys Lys Leu Asp Lys Gln Tyr Glu Ser
            690                 695                 700

Leu Ser Leu Phe His Pro Ser Asn Val Glu Met Leu Ser Ser Met Asp
705                 710                 715                 720

Ser Ala Ser Val Arg Ile Ile Lys Pro Phe Pro Ala Pro Gln Thr Pro
            725                 730                 735

Gly Arg Leu Gln Pro Ala Pro Val Ile Pro Ser Ala Pro Ala Ala Pro
            740                 745                 750

Lys Leu Asp His Gln Arg Met Asp Thr Ile Gln Glu Asp Pro Ser Thr
            755                 760                 765

Asp Ser His Met Asp Glu Asp Gly Phe Glu Lys Asp Pro Phe Pro Asn
770                 775                 780

Ser Ser Thr Ala Ala Lys Ser Phe Glu Asp Leu Thr Asp His Pro Val
785                 790                 795                 800

Thr Arg Ser Glu Lys Ala Ala Ser Phe Lys Leu Gln Arg Gln Asn Arg
            805                 810                 815

Val Asp Ser Lys Glu Thr Glu Cys
            820

<210> SEQ ID NO 20
<211> LENGTH: 5
<212> TYPE: PRT
<213> ORGANISM: Artificial sequence
<220> FEATURE:
<223> OTHER INFORMATION: Synthetic sequence: Peptide sub-sequence of
      fluorogenic substrate

<400> SEQUENCE: 20

Lys Pro Leu Gly Leu
1               5
```

ANTI-TACE ANTIBODY MOLECULES AND THEIR USES

CROSS-REFERENCE TO RELATED APPLICATIONS

This application is the U.S. National Stage of International Application No. PCT/GB2012/000095, filed Jan. 30, 2012, which claims the benefit of U.S. Provisional Patent Application No. 61/438,354, filed Feb. 1, 2011. The entire disclosure of each of the aforesaid applications is incorporated by reference in the present application.

FIELD OF THE INVENTION

The present invention relates to anti-TNF-α Converting Enzyme (TACE) antibody molecules and their uses, and more particularly to anti-TACE antibody molecules that are capable of inhibiting a biological activity of TACE by binding to its catalytic domain and Dis-Cys domain.

BACKGROUND OF THE INVENTION

TNF-α Converting Enzyme (TACE) (also known as A Disintegrin And Metalloprotease 17 (ADAM17)), is a membrane-bound metalloprotease responsible for cleaving a variety of pathologically significant substrates. Initially identified as the enzyme responsible for solubilising membrane-associated pro-TNF-α, a process subsequently termed "ectodomain shedding", TACE has since proved capable of cleaving a wide range of substrates, such as epidermal growth factor receptor (EGFR) ligands, extracellular Notch, cell-surface receptors and adhesion molecules. As proteolytic cleavage is an indispensable activation event for many of these substrates, TACE has emerged as an attractive therapeutic target for the treatment of cancer and rheumatoid arthritis. The role of TACE is reviewed in Murphy (Nature Reviews: Cancer, 8(12): 929-941, 2008).

A role for TACE in regulating TNF-α and hence the potential utility of inhibiting TACE as a therapeutic strategy for treating inflammatory disease has been recognised for some time and many companies have tried to develop small molecule inhibitors of TACE. However, the metalloprotease family are highly conserved and developing selective small molecule inhibitors has proven to be a significant challenge. Early trials using broader spectrum metalloprotease inhibitors were prone to toxicity issues and as such the ability to generate selective inhibitors of this family is desirable, see Moss et al (Nature Clinical Practice, 4(6): 300-309, 2008).

An alternative strategy to developing a selective TACE inhibitor would be to utilise the selectivity that is generally achievable with antibodies. However, while antibodies which bind to TACE have been reported and are commercially available, unusually none of these to date have had antagonistic activity. By way of example of this, while WO 96/041624 discloses the identification of TACE enzyme and suggests producing anti-TACE antibodies, no antibodies are disclosed in the application, still less antibodies having specific functional properties such as antagonist antibodies. This in turn means that the development of antibody based therapeutics capable of blocking TACE activity remains an unsolved problem in the art.

SUMMARY OF THE INVENTION

Broadly, the present invention is based on the realisation that a holistic multi-domain approach to the production of antibodies may be used to specifically inhibit complex proteases, such as TACE. This insight was then employed to produce antibody molecules capable of binding to TACE and, for the first time in the art, of acting as antagonists of one or more its biological activities.

Without wishing to be bound by any particular theory, the inventors believe that the antibody molecules of the present invention have an antibody binding mode that is unique in that it binds to TACE in a cross domain binding mode. As supported in the examples, this means that residues in both the catalytic domain and in the cysteine rich/disintegrin domains (Dis-Cys) are involved in antibody binding to TACE, helping to improve the specificity of the antibody binding and/or helping to improve inhibition of TACE biological activity.

The antibody molecules of the present invention were designed following the inventors' insight that the catalytic domain and Dis-Cys domain are spatially associated within the complete ADAM ectodomain, and in particular that the "C-shape" of TACE means that the TACE non-catalytic carboxyl-terminal Dis-Cys domain partially obstructs macromolecular access to the amino-terminal catalytic domain. This in turn led the present inventors to conclude that a selective TACE inhibitor could utilise this spatially connected multi-domain topology by broadly antagonising the catalytic domain, whilst simultaneously sourcing additional specificity from local Dis-Cys residues.

As described in more detail below, the inventors exploited ADAM multi-domain topology by first isolating an inhibitory human antibody (D1) that bound TACE non-catalytic regions exclusively through its variable heavy ($V_H$) domain. A D1-$V_H$ biased scFv phage-display library was then used to selectively isolate a new variable light ($V_L$) chain that could simultaneously bind to the TACE catalytic domain. The resulting "cross-domain" human antibody (D1(A12)) is the first holistic ADAM ectodomain inhibitor and is the most selectively potent cell surface TACE inhibitor ever described.

Accordingly, in a first aspect, the present invention provides an isolated antibody molecule which specifically binds to TNF-α Converting Enzyme (TACE) and inhibits a biological activity of TACE. As explained above, the present inventors believe that the antibody molecules of the present invention are capable of inhibiting a biological activity of TACE by binding to both the catalytic domain and the Dis-Cys domain of TACE. By way of example, the antibodies of the present invention are preferably capable of inhibiting cleavage of a substrate by TACE. Other features and properties of the antibodies are described below.

In a further aspect, the present invention provides a pharmaceutical composition comprising an antibody molecule as disclosed herein and a pharmaceutically acceptable excipient.

In a further aspect, the present invention provides an antibody molecule as disclosed herein for use in a method of treatment of the human or animal body.

In a further aspect, the present invention provides an antibody molecule as disclosed herein for use in a method of treatment of a TACE-mediated condition.

In a further aspect, the present invention provides the use of an antibody molecule as disclosed herein in the manufacture of a medicament for use in treating a TACE-mediated condition.

In a further aspect, the present invention provides a method of treating an individual with a TACE-mediated condition comprising administering an antibody molecule as disclosed herein to an individual in need thereof.

In the medical uses and methods of treatment of the present invention, preferably the TACE-mediated condition is cancer, an immune related disorder, or psoriasis, and more particularly a cancer such as brain cancer, breast cancer, colon cancer, gastric cancer, kidney cancer, liver cancer, lung cancer, ovarian cancer, pancreatic cancer, prostate cancer or colorectal cancer, an immune related disorder such as rheumatoid arthritis, or an inflammatory or allergic based disease such as asthma.

In a further aspect, the present invention provides a method of producing an antibody molecule which specifically binds to an ADAM family metalloproteinase, wherein the antibody is capable of inhibiting the protease activity of the ADAM family metalloproteinase by binding to both the catalytic domain and the Dis-Cys domain of the metalloproteinase, the method comprising:

(a) identifying an antibody comprising a variable heavy chain domain capable of binding to the ADAM family metalloproteinase polypeptide comprising the catalytic domain and the Dis-Cys domain, wherein the catalytic domain is bound to an inhibitor of the ADAM family metalloproteinase;

(b) identifying an antibody comprising a variable light chain domain capable of binding to the isolated catalytic domain of the ADAM family metalloproteinase; and (c) producing an antibody molecule comprising the variable heavy chain domain identified in step (a) and the variable light chain domain identified in step (b). A description of ADAM family metalloproteinases and references to their sequences and structure is provided in Murphy et al, Nature Reviews: Cancer, 8: 929-941, 2008. This describes how the ADAM family metalloproteinases share a common domain structure that includes Dis-Cys and catalytic domains. Examples of ADAM family metalloproteinases and their alternative names include, but are not limited to ADAM8 (Ms2, CD156a), ADAM9 (Meltrin-γ, MDC9), ADAM10 (Kuzbanian, MADM, sU17), ADAM12 (Meltrin-α), ADAM15 (Metargidin, MDC15), ADAM17 (TACE), ADAM19 (Meltrin-β, MADDAM), ADAM28 (MDCL, eMDCII, TECADAM) and ADAM33.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 1. Experimental overview. (A) The human TACE ectodomain consists of an amino-terminal metalloprotease catalytic domain (light red) and a carboxyl-terminal non-catalytic Dis-Cys domain (light blue) (I-TASSER model). We exploited this multi-domain topology to develop the first truly specific ADAM inhibitor using two-step antibody phage display. (B) (i) First, the catalytic site of TACE ectodomain was blocked during primary antibody phage display selections using the small molecule inhibitor CT1746. This prevented the selection of antibodies with catalytic cleft epitopes that could cross-react with non-target metalloproteases. (ii) Primary screening revealed the inhibitory scFv antibody clone D1. This scFv bound specifically to the TACE Dis-Cys domain through its variable heavy ($V_H$) domain. (iii) A D1-$V_H$-bias antibody phage display library was produced to introduce new variable light (neo-$V_L$) chains whilst maintaining the TACE specificity provided by the D1-$V_H$. Secondary selections were performed in the absence of CT1746 in order to provide the neo-$V_L$ chains with uninterrupted access to the TACE catalytic site. (iv) Secondary screening identified several neo-$V_L$ scFvs capable of binding the isolated TACE catalytic domain. Due to Dis-Cys domain binding through the D1-$V_H$ these "cross-domain" antibodies maintained their strict specificity for TACE. D1-$V_H$-neo-$V_L$ scFv clone A12 (hereafter D1(A12)) exhibited the highest affinity for the TACE ectodomain and is the most selectively potent cell surface ADAM inhibitor ever described.

Figure 2:
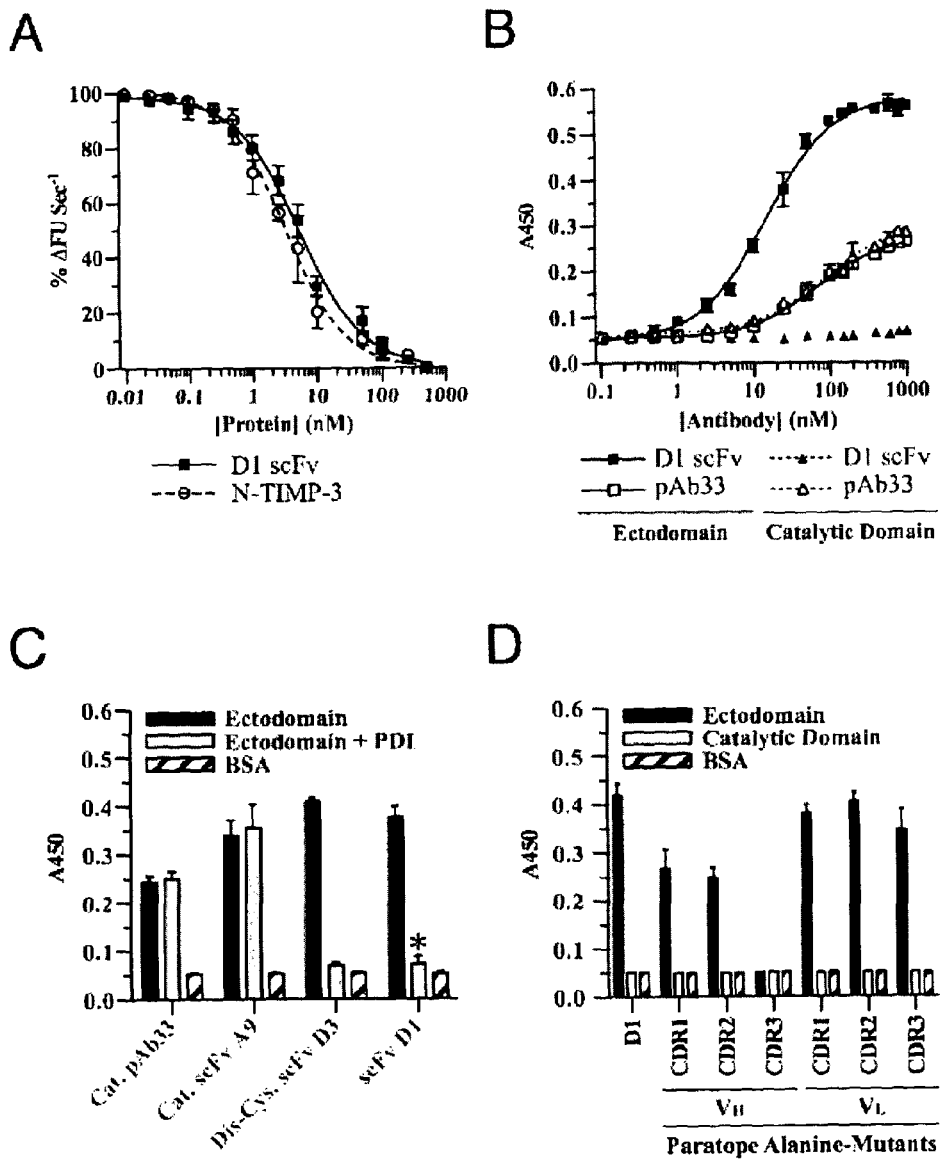
FIG. 2. ScFv D1 is a $V_H$-dependent TACE ectodomain inhibitory human antibody. (A) Recombinant human TACE ectodomain ($Arg^{215}$-$Arg^{651}$) was pre-incubated with titrated concentrations of either human D1 scFv or the N-terminal fragment of the natural TACE inhibitor, N-TIMP-3. Subsequent TACE proteolytic activity was measured in a quenched fluorescent peptide cleavage assay. D1 inhibits TACE ectodomain proteolysis with comparable potency to N-TIMP-3 ($ICS_{50}^{D1}$=5.4 (±0.4) nM; $IC_{50}^{N\text{-}TIMP\text{-}3}$=3.2 (±0.2) nM)). (B) Immobilised TACE ectodomain and catalytic domain ($Arg^{215}$-$Ser^{474}$) were probed with titrated concentrations of scFv D1 and the anti-catalytic domain rabbit polyclonal antibody pAb33. Despite its capacity to inhibit TACE-mediated peptide hydrolysis, D1 scFv failed to bind the isolated TACE catalytic domain. (C) We have previously described how Protein Disulphide Isomerase (PDI) can re-arrange TACE Dis-Cys domain disulphide bonds. The binding of TACE catalytic domain antibodies pAb33 and scFv A9 remain unaltered by PDI treatment of the TACE ectodomain. In contrast, Dis-Cys scFv D3 and scFv D1 lose all immunoreactivity following PDI treatment (*). (D) Paratope scanning mutagenesis of scFv D1 CDRs revealed the $V_H$-domain was primarily responsible for TACE ectodomain binding. In contrast, the D1 $V_L$-domain appeared almost entirely dispensable for TACE ectodomain binding.

$K_D^{Ecto}$=0.03). In contrast, the cross-domain D1(A12) FAb shows a >10-fold affinity preference for the complete ectodomain ($K_D^{Ecto}$=461 (±65) pM) over the isolated catalytic domain ($K_D^{Cat}$=5,210 (±102) pM) ($\Delta K_D$=11.3). (D) Inverted D1(A12) ELISA studies produced a comparable >10-fold affinity divergence ($EC50^{D1(A12):Ecto}$=920 (±19) pM; $EC_{50}^{D1(A12:Cat)}$=11,120 (±94) pM) ($\Delta EC_{50}^{(A12)}$= $EC_{50}^{D1(A12):Cat}/EC_{50}^{D1(A21):Ecto}$=12.1). All ±represent SD.

FIG. 4. D1(A12) paratope scanning mutagenesis. (A) All D1(A12) scFv paratope residues extending beyond the β-carbon were individually mutated to alanine (n=30), expressed in E. coli and affinity-purified. The $IC_{50}$ for each mutant against both the complete TACE ectodomain ($IC_{50}^{Ecto}$) and the isolated catalytic domain ($IC_{50}^{Cat}$) were determined in solution by quenched-fluorescent peptide assay. In addition, the "wild-type" D1(A12) scFv $IC_{50}$ ($IC_{50}^{WT}$) was simultaneously calculated for both the TACE ectodomain ($IC_{50}^{Ecto:WT}$) and catalytic domain ($IC_{50}^{Cat:WT}$) using an identical procedure. The subsequent change in Gibb's free energy ($\Delta\Delta G$) was calculated ($\Delta\Delta G$=+RT1n($IC_{50}^{Ala}/IC_{50}^{WT}$)) for each mutant and antigen. Whilst many mutations proved detrimental to the D1(A12) $IC_{50}^{WT}$ for both antigens, several appeared to specifically alter binding to either the TACE ectodomain (*) or the catalytic domain (=). Correlating with paratope mutagenesis of scFv D1 (FIG. 1(C)), several residues in the D1(A12) variable-heavy chain ($V_H$) contribute to $IC_{50}^{Ecto:WT}$. Interestingly, residues SH31, YH32 and SH52 (*) (Kabat numbering) exclusively support $IC_{50}^{Ecto:WT}$ and appear relatively dispensable for achieving $IC_{50}^{Cat:WT}$. In contrast, several variable-light ($V_L$) chain residues contribute significantly to $IC_{50}^{Cat:WT}$ (QL27, SL28, IL29, SL91 and FL92 (=))—yet appear dispensable for achieving $IC_{50}^{Cat:WT}$. When mapped onto D1(A12) Fv models (26) (employing colours detailed on the right y-axis), residues displaying a $IC_{50}^{Cat:WT}$ antigen bias cluster at polar ends of the paratope (dashed white lines). (B) The $EC_{50}$ for each paratope mutant was calculated by solid-phase ELISA and used to calculate ΔΔG (ΔΔG=+RT1n($EC_{50}^{Ala}$/$EC_{50}^{WT}$). Echoing the pattern described in (A), residues SH31, YH32 and SH52 (*) support $EC_{50}^{Ecto:WT}$, and residues QL27, SL28, IL29, SL91 and FL92 (=) support $EC_{50}^{Cat:WT}$. In addition to residues displaying a specific antigen $EC_{50}$ bias, all alanine mutants within CDR-H3 disrupted binding to both antigens.

FIG. 5. D1(A12) is a potent inhibitor of TACE ectodomain proteolysis. (A) Either 100 nM TACE complete ectodomain or isolated catalytic domain were combined with 5 μM GST-TNF-α and titrated concentrations of D1(A12) FAb. After incubating at 37° C., each reaction was resolved by SDS-PAGE, coomassie stained and individual bands were quantified by densitometry. Quantitative results from three separate experiments are displayed as a percentage of a 50 μM CT1746 (CT) metalloprotease inhibitor control. D1(A12) FAb inhibited the cleavage of recombinant TNF-α by both the TACE ectodomain ($IC_{50}^{Ecto}$=73.9 (±3.2) nM) and to a lesser potency, the isolated catalytic domain ($IC_{50}^{Cat}$=124.7 (±6.2) nM). (B) Recombinant human TACE ectodomain and catalytic domain were individually pre-incubated with titrated concentrations of D1(A12) FAb and the N-terminal fragment of the catalytic-cleft focussed TACE inhibitor, N-TIMP-3. Subsequent proteolytic activity was measured in a quench fluorescent peptide cleavage assay. D1(A12) FAb inhibited the proteolytic capacity of the TACE catalytic domain with a comparable potency to N-TIMP-3. However, when the full-length recombinant human TACE ectodomain was pre-incubated with both inhibitors, the D1(A12) FAb proved >5-fold more potent than N-TIMP-3 (=). (C) Cancer cells with known expression of TACE substrates (TOV21G: TNF-α, IGROV1: TGF-α, PC3: AREG) and HeLa cells stably over expressing HB-EGF-Alkaline Phosphatase were used to assay cell surface TACE activity. Each cell line was stimulated with PMA following a 1 hour pre-treatment with various concentrations of either D1(A12) human IgG1, N-TIMP-3 or control human plasma IgG. Soluble TACE products were quantified from conditioned medium by sandwich ELISA or alkaline phosphatase activity. D1(A12) IgG1 consistently inhibited cell surface TACE activity around 5-fold more potently than N-TIMP-3 (*). Cell surface TACE inhibition directly correlates with the enzymatic data in (B) (i.e. *≈=). Full $IC_{50}$ data can be found in Supplementary Table 1.

FIG. 6. Predicted TACE ectodomain topology (A) A 1-dimensional depiction of TACE ectodomain (construct $Arg^{651}$) illustrating the relative locations of the Signal Peptide (S; white), Pro Domain (green), Furin cleavage site (hollow arrow), Catalytic Domain (red), zinc-coordinating histidines and the Disintegrin-Cysteine Rich (Dis-Cys) Domain (blue). (B) A 3-dimensional representation of TACE homologs employing the colour system outlined in (A). The crystal structure of the ADAM-homolog Russell's Viper Venom metalloprotease (RVV-X) reported the tight spatial association between the catalytic and Dis-Cys domains. In combination with earlier vascular apoptosis-inducing protein (VAP) crystallography, this structural evidence supported the notion that ADAMs are "C-shaped". More recently, the non-catalytic human ADAM22 ectodomain structure (complete with carboxyl-terminal EGF-like domain, yellow) has continued this idea. (C) The structural homology modelling of TACE (Edwards et al, 2008) reveals the full ectodomain likely exists in a comparable "C-shape". Such models suggest that the Dis-Cys domain obstructs macromolecular access to the TACE catalytic site in a similar fashion to RVV-X and ADAM22. The close association between the Dis-Cys domain and the catalytic cleft could explain why the complete TACE ectodomain is ~10-fold less proteolytic than the isolated catalytic domain. Moreover, this topology might also explain why the natural protein inhibitor of TACE (and many other metalloproteases), Tissue Inhibitor of Metalloprotease 3 (TIMP-3), is significantly better at inhibiting the exposed TACE catalytic domain rather than the "guarded" full ectodomain.

FIG. 7. Isolation of anti-TACE ectodomain human scFv antibodies. (A) Following two rounds of solution-phase phage display selections against biotinylated TACE ectodomain (with CT1746), the eluted phagemid population was transferred into the pSANG10-3F vector and individual scFvs were expressed in *E. coli*. Each antibody was ELISA-screened against TACE ectodomain (without CT1746) and BSA. Results are expressed as the fold-difference between the two antigens (ΔA450=$A450^{TACE}$/$A450^{BSA}$). All clones ΔA450≥10 (dashed line) were isolated, sequenced to remove replicates, individually expressed and purified by affinity chromatography. In addition, a negative control clone (B9) was also advanced. (B) Titration ELISAs against TACE ectodomain revealed $EC_{50}$s ranging between 11-420 nM. (C) Quenched-fluorescent (QF) peptide activity of 1 nM recombinant TACE ectodomain following pre-incubation with 500 nM purified lead antibody revealed several scFvs possessed some inhibitory capacity (*). (D) To investigate the translation of QF-peptide inhibition to cell surface TACE inhibition, HeLa cells over-expressing alkaline-phosphatase (AP) tagged HB-EGF were pre-incubated with 500 nM of each scFv and stimulated with PMA. PBS and the amino-terminal domain of the endogenous TACE inhibitor TIMP-3, N-TIMP-3 (NT3), were used as positive and negative and respectively. TACE-mediated shedding of HB-EGF was measured by assaying AP activity from the conditioned media (displayed as A405). Despite the identification of several recombinant TACE ectodomain inhibitors in (C), only scFv D1 (**) appeared to retain this inhibitory potency at the cell surface. All ±represent SD.

FIG. 8. D1 scFv is selective for TACE. (A) 500 nM immobilised human TACE ectodomain, human TACE catalytic domain, mouse TACE ectodomain, human ADAM10 ectodomain, human ADAM12 ectodomain and BSA were individually ELISA probed with 100 nM D1 scFv, anti-TACE catalytic domain polyclonal (pAb28233) and anti-ADAM10 polyclonal (pAb10956). Despite the close sequence homology between the ADAM antigens, D1 scFv appeared entirely selective for human TACE ectodomain. (B) Recombinant human ADAM10 ectodomain was pre-incubated with titrated concentrations of either human D1 scFv or the small molecule metalloprotease inhibitor, CT1746. Subsequent ADAM10 proteolytic activity was measured in a quench fluorescent peptide cleavage assay. Results are expressed as the percentage of an untreated control. Whilst CT1746 rapidly inhibits ADAM10 proteolysis, scFv D1 has no effect. All ±represent SD.

FIG. 9. D1(A12) shares a common epitope with N-TIMP-3. (A) 100 nM TACE ectodomain was immobilised onto an ELISA plate and pre-incubated with various concentrations of D1(A12) monovalent FAb. The subsequent accessibility of the TACE active site was monitored by assaying for N-TIMP-3 binding. D1(A12) blocks access to the TACE ectodomain active site at 1:1 molar ratio. (B) Reversing the probe orientation (i.e. TACE pre-incubated with various concentrations of N-TIMP-3 and probed with D1(A12) FAb) produced comparable results. All ±represent SD.

Figure 10:
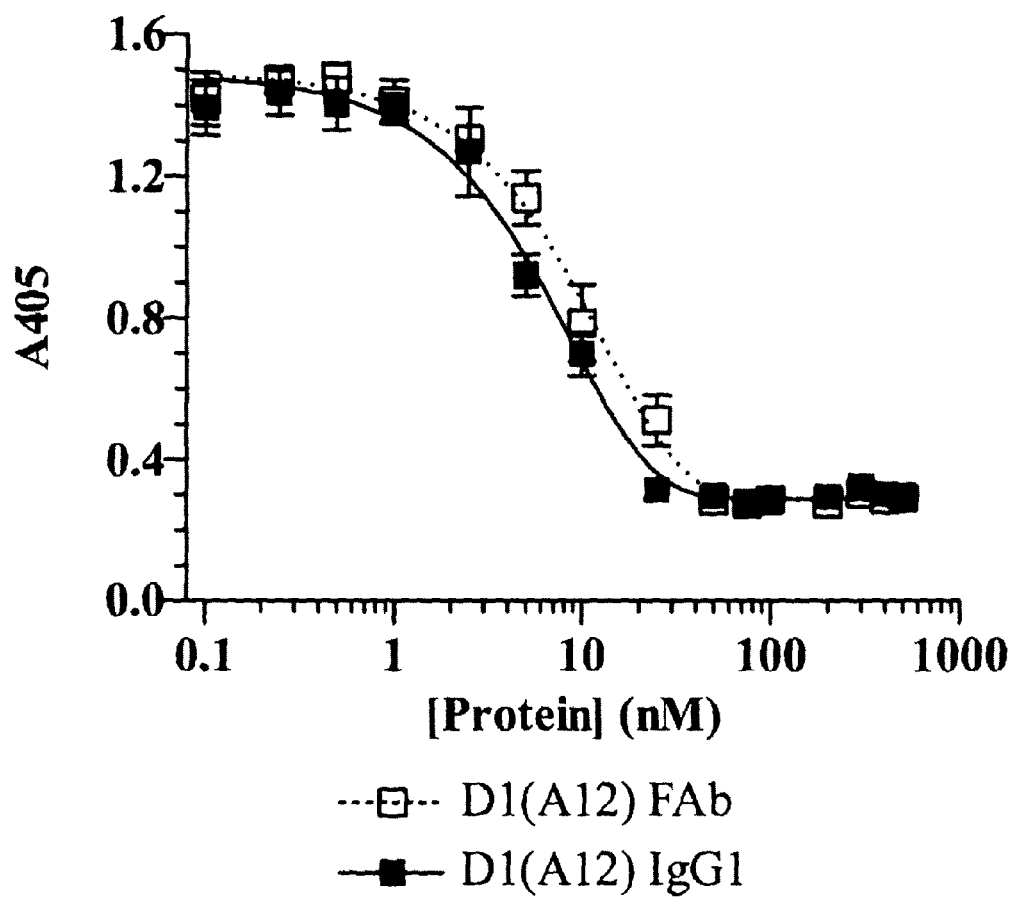

FIG. 10. D1(A12) IgG and FAb inhibition of cell surface TACE. To investigate whether the bivalent nature of D1(A12) IgG1 influenced its TACE inhibitory potency, titrations of IgG1 and monovalent FAb were compared in a PMA stimulated HeLa alkaline-phosphatase (AP) tagged HB-EGF assay. The D1(A12) FAb displayed a comparable inhibitory profile to the IgG1. This suggested only one variable domain of each IgG1 was responsible for inhibiting cell surface TACE. All ±represent SD.

FIG. 11. D1(A12) is a selective TACE inhibitor. (A) 50 nM immobilised human TACE ectodomain, human TACE catalytic domain, mouse TACE ectodomain, human ADAM10 ectodomain, human ADAM12 ectodomain and BSA were individually ELISA probed with 100 nM D1(A12) FAb, anti-TACE catalytic domain polyclonal (pAb28233) and anti-ADAM10 polyclonal (pAb10956). Despite the close sequence homology between the ADAM antigens, D1(A12) FAb appeared entirely selective for human TACE. (B) Recombinant human ADAM10 ectodomain was pre-incubated with titrated concentrations of either human D1(A12) FAb or the small molecule metalloprotease inhibitor, CT1746. Subsequent ADAM10 proteolytic activity was measured in a quench fluorescent peptide cleavage assay. Despite partially binding the TACE catalytic domain, D1(A12) FAb has no effect on ADAM10 activity. (C) MCF7 cells stably transfected with alkaline phosphatase tagged HB-EGF provide a useful model to distinguish between ADAM10 and TACE cell surface shedding activity. Western blot analysis of MCF7 breast cancer cell lysates following treatment with non-targeting, ADAM10 or TACE siRNA. (D) PMA-stimulation of MCF7 cells results in TACE dependent shedding of HB-EGF-AP. (E) Ionomycin-stimulation of MCF7 cells results in ADAM10 dependent shedding of HB-EGF-AP. (F) D1(A12) IgG1 only inhibits TACE-mediated PMA stimulation of HB-EGF-AP shedding in MCF7 breast cancer cells. For cell assays, one-way ANOVA tests were performed comparing control cells (e.g. non-targeting siRNA) to variable (e.g. PMA stimulated). P-values: *=<0.05, =<0.01, *=<0.001. All ±represent SD.

Figure 12:
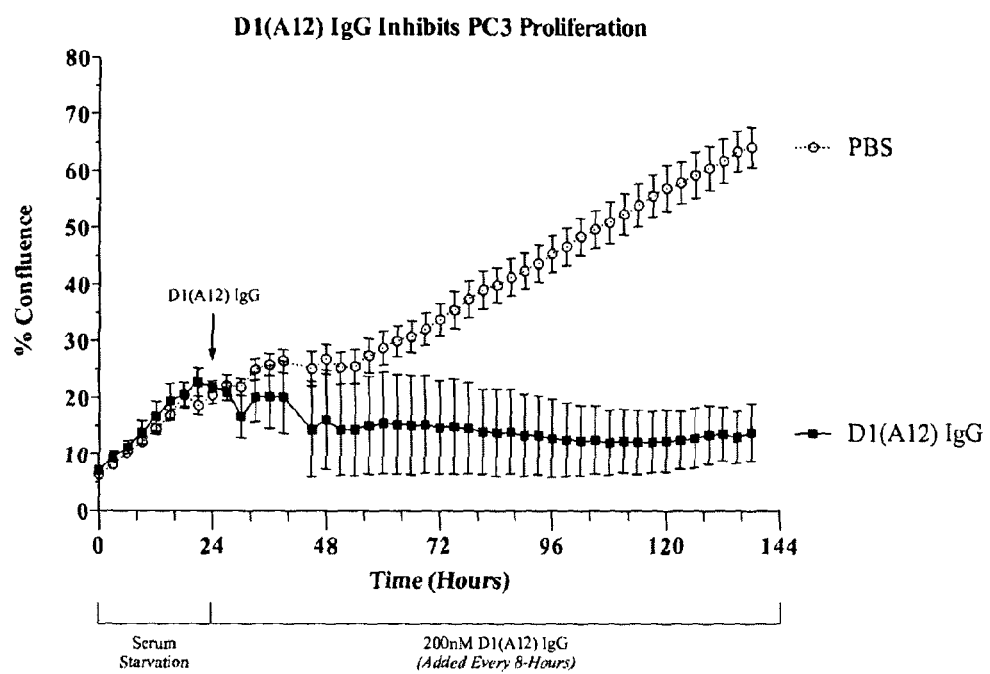

FIG. 12. PC3 cells were seeded at ~10% confluence and grown in serum-free medium for 24 hours. Either 200 nM D1(A12) IgG1 or an equal volume of PBS were added to the medium every 8-hours. Confluence was measured using IncuCyte. TACE inhibition by D1(A12) IgG1 severely disrupts serum-free proliferation of PC3 cells. Error bars represent S.D.

Figure 13:
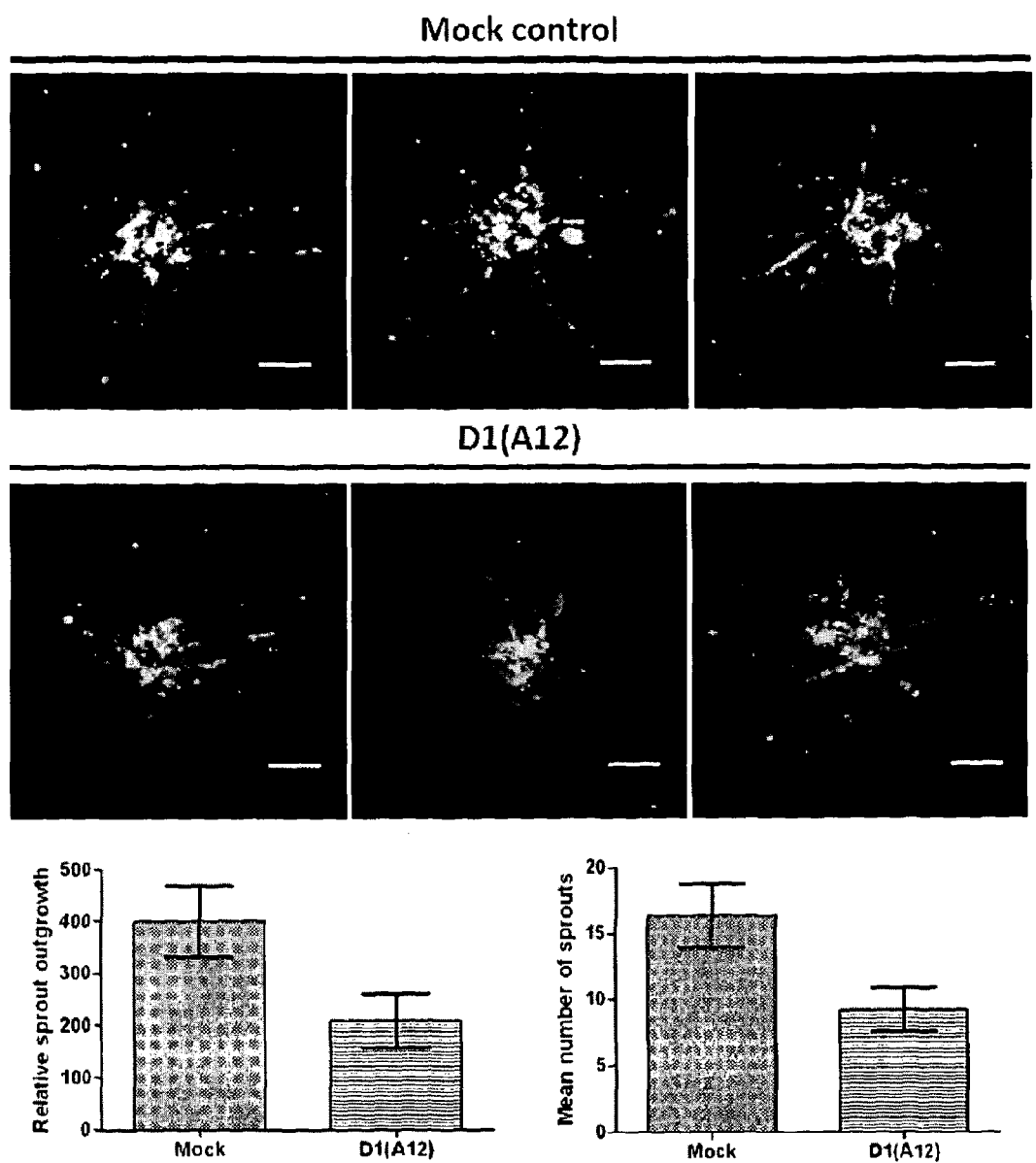

FIG. 13. Multicellular 3 dimensional spheroids comprising endothelial cells, fibroblasts and MDA-MB-231 breast cancer cell lines were incubated in type-I collagen with either 330 nM D1(A12) IgG1 or an equal volume of PBS. After 36 h incubation, endothelial cells pre-dyed with a green CMFDA CellTracker dye were imaged and endothelial sprout formation was quantified for total outgrowth and number of sprouts. Both parameters show a decrease in endothelial cell sprout formation when TACE was inhibited by D1(A12). White bars correspond to 100 µm.

Figure 14:
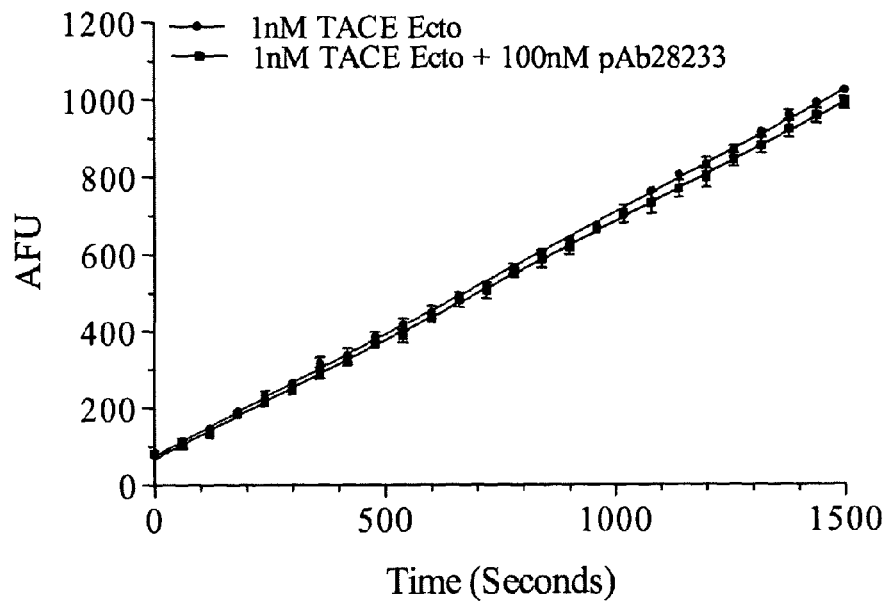

FIG. 14. Recombinant TACE ectodomain was pre-incubated either alone or with 100 nM pAb28233 (anti-catalytic domain polyclonal antibody) for 1 hour. Subsequent proteolytic activity was detected using a quenched-fluorescent peptide assay. Despite binding to the TACE catalytic domain, pAb28233 does not inhibit TACE activity.

Figure 15:
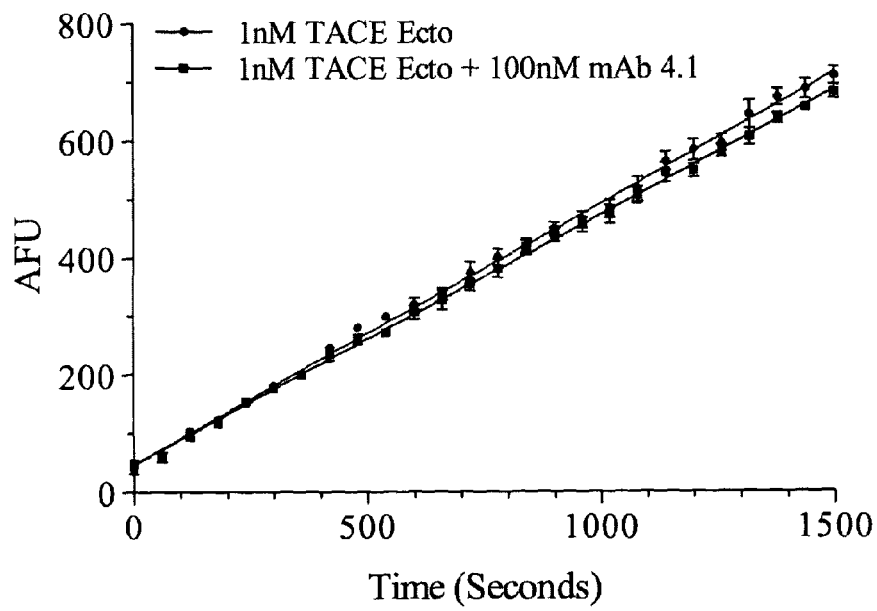

FIG. 15. Recombinant TACE ectodomain was pre-incubated either alone or with 100 nM mAb 4.1 (anti-catalytic domain monoclonal antibody) for 1 hour. Subsequent proteolytic activity was detected using a quenched-fluorescent peptide assay. Despite binding to the TACE catalytic domain, mAb 4.1 does not inhibit TACE activity.

Figure 16:
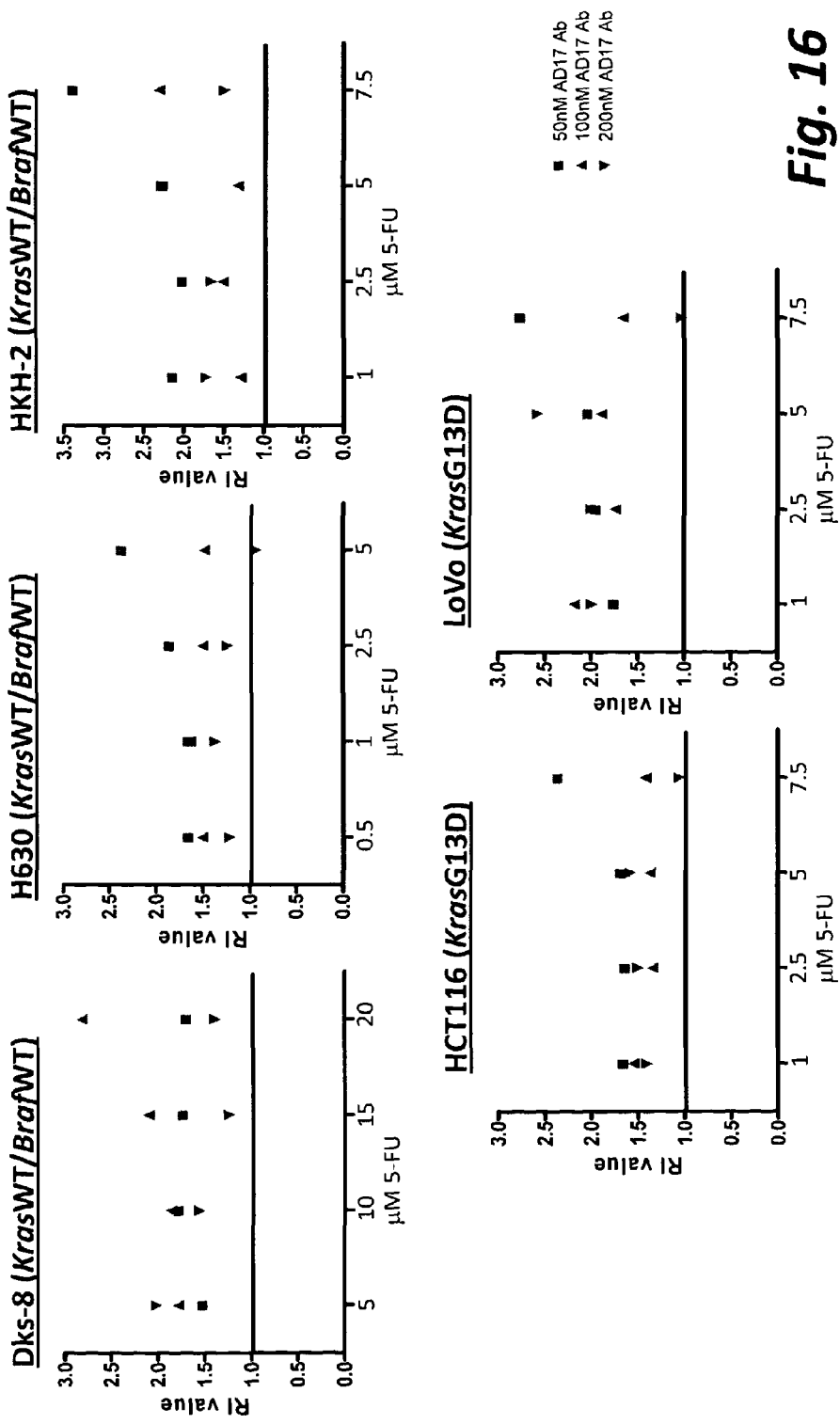

FIG. 16. Anti-TACE antibody D1(A12) sensitizes KrasWT and KrasMT colorectal cancer cells to chemotherapy treatment.

Figure 17:
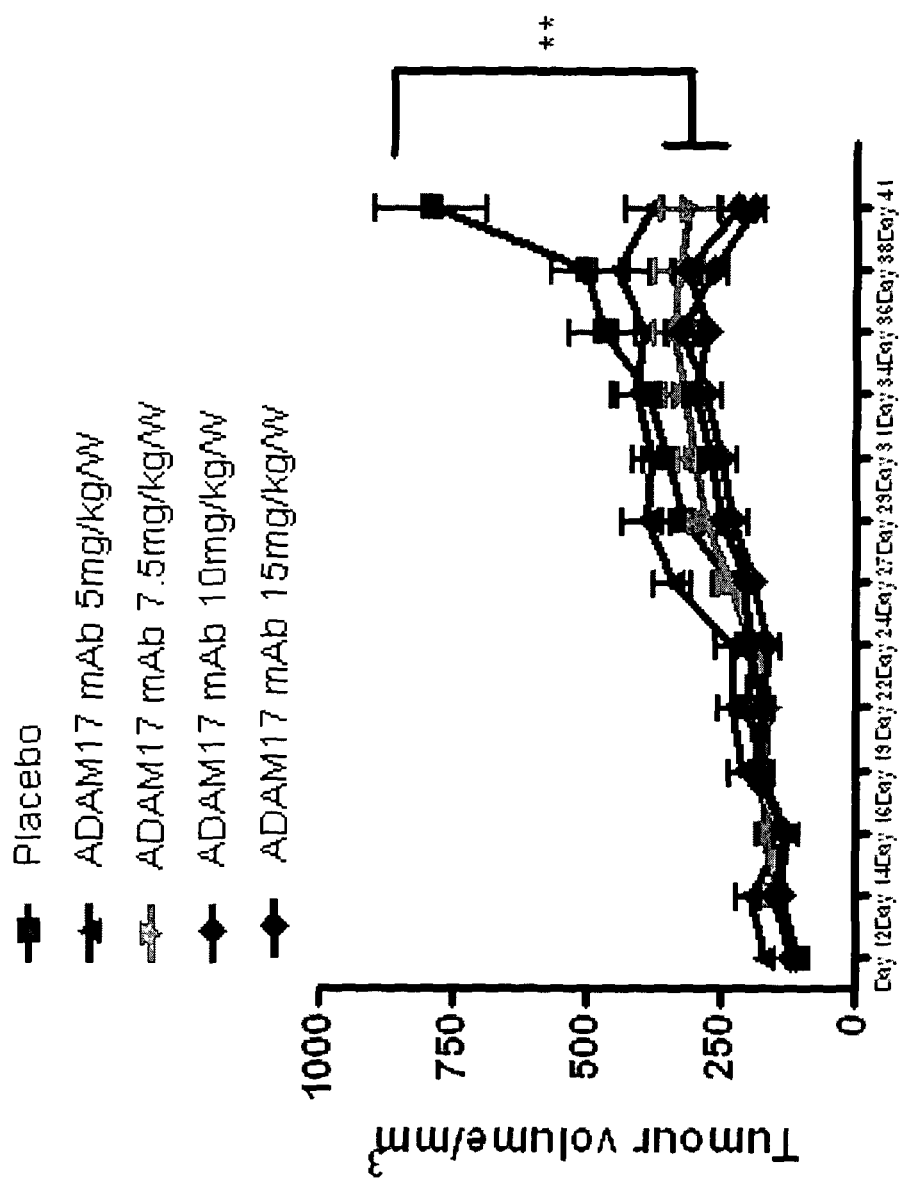

FIG. 17 Anti-TACE antibody abrogates colorectal xenograft (H630) growth in vivo.

Figure 18:
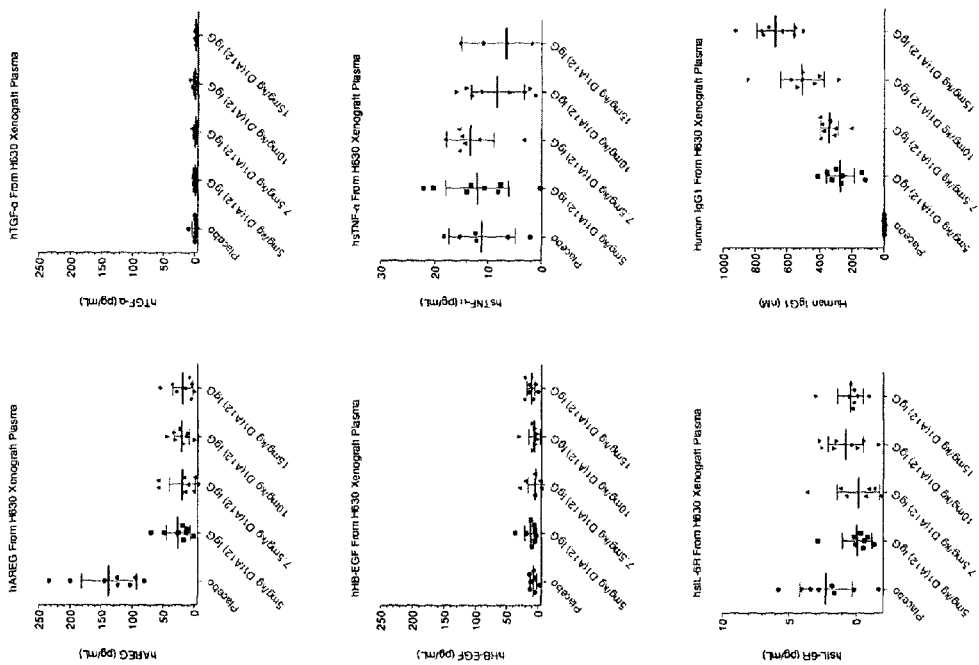

FIG. 18. Monitoring plasma levels of potential TACE substrates in a colorectal cancer xenograft.

Figure 19:
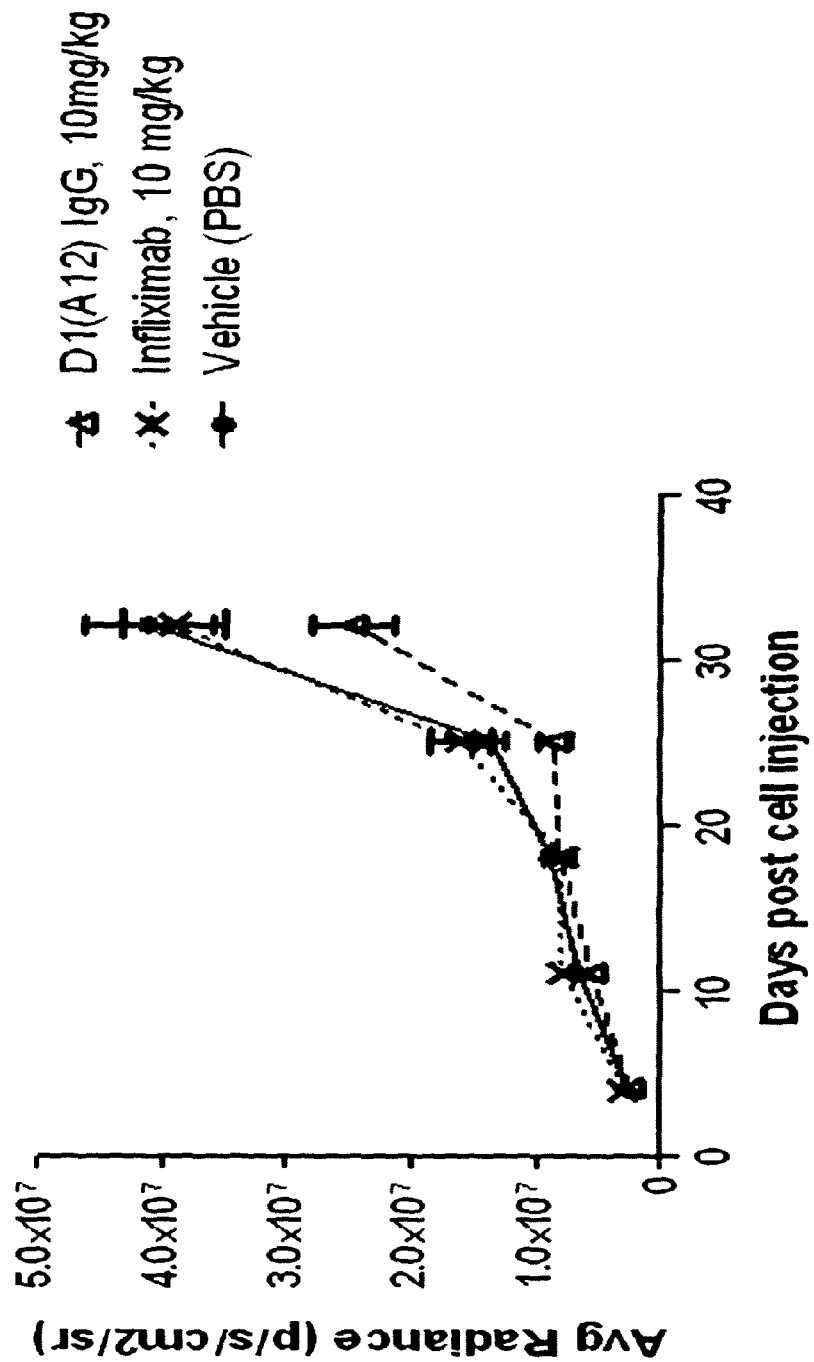

FIG. 19. Testing of anti-TACE antibody in an IGROV1 ovarian cancer xenograft model.

Figure 20:
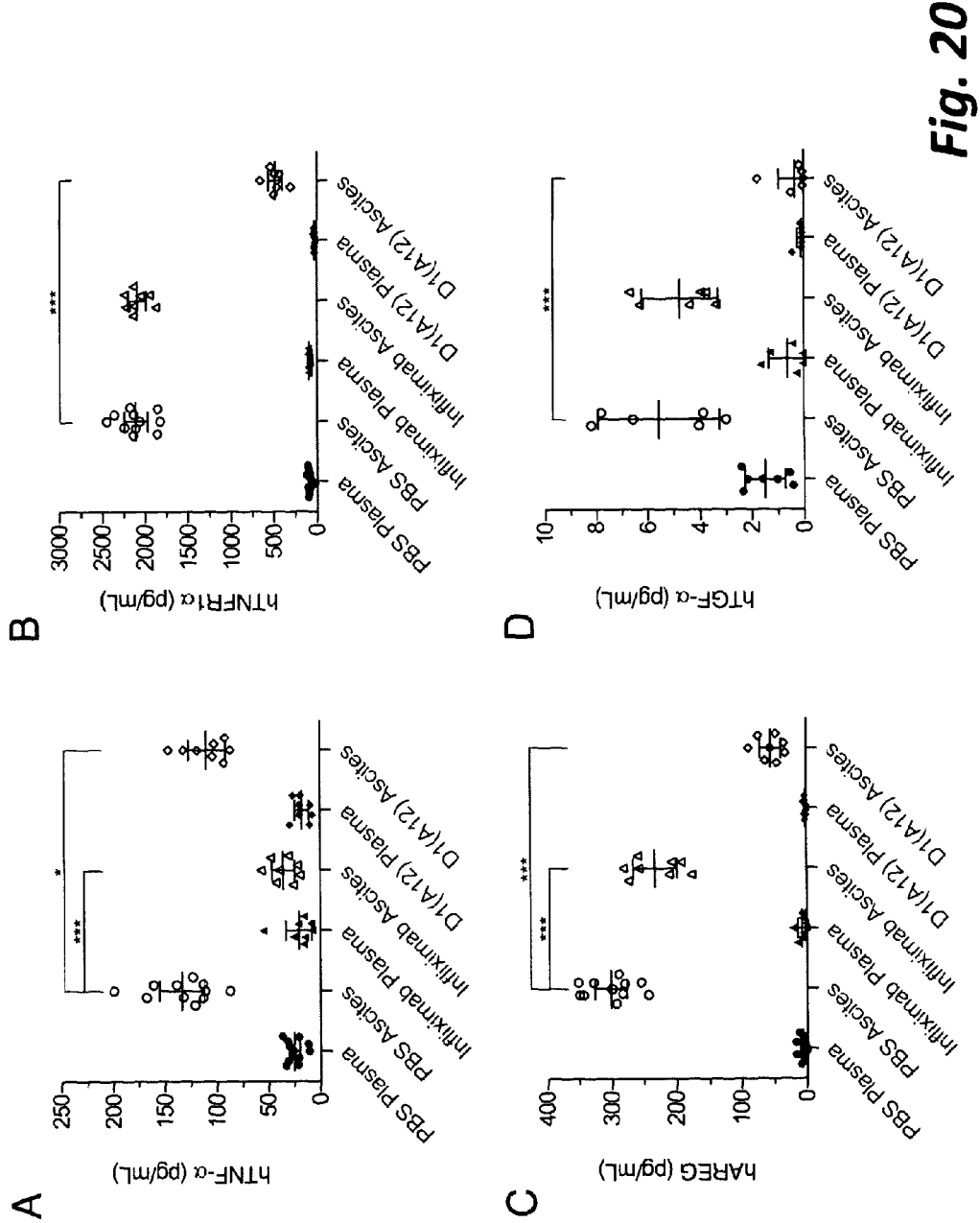

FIG. 20. Monitoring plasma/ascites levels of potential TACE substrates in an IGROV1 ovarian cancer xenograft model.

Figure 21:
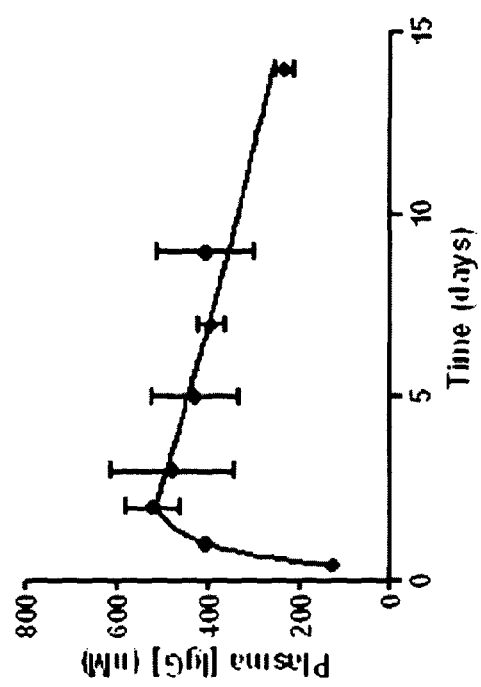

FIG. 21. Pharmacokinetics of anti-TACE antibody D1(A12) in nude mice after a single dose of 10 mg/kg i.p. N=2 or more mice per time point. Error bars represent the standard error of the mean.

DETAILED DESCRIPTION

Anti-TACE Antibody Molecules

Figure 6:
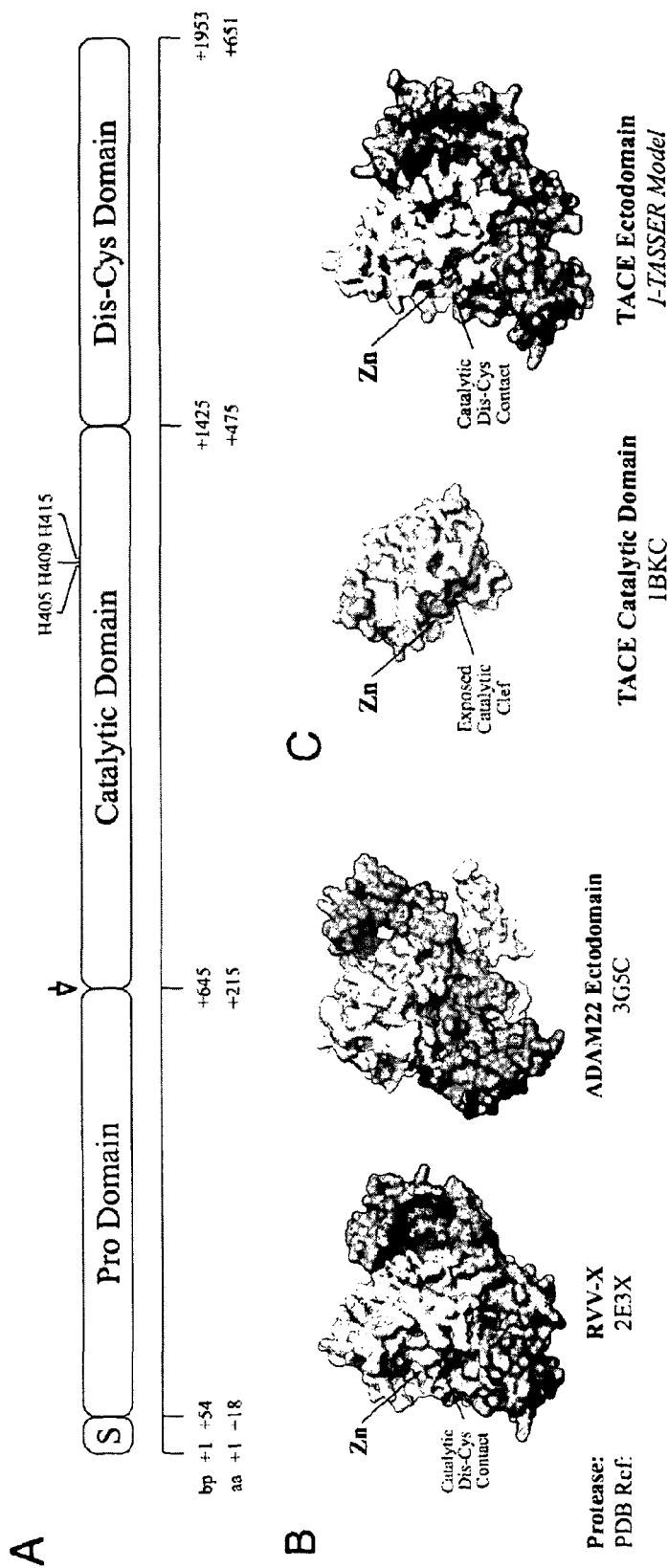

Unless stated otherwise, antibody residues are numbered herein in accordance with the Kabat numbering scheme. The structure and domain of TACE are set out in FIG. 6 and amino acid sequence of TACE is set out as SEQ ID NO: 19. Preferably, the antibody molecules of the present invention are capable of binding to TACE polypeptides that comprise a polypeptide having at least 80% sequence identity to amino acids 215 to 651 as set out in SEQ ID NO: 19, or a fragment thereof, wherein the fragment is biologically active.

In some embodiments, the antibody molecules of the present invention comprise one or more of the following CDR sequences:

(a) a CDR-H1 having the amino acid sequence of SEQ ID NO: 1, or the amino acid sequence of SEQ ID NO: 1 with one or more amino acid substitutions, deletions or insertions; and/or
(b) a CDR-H2 having the amino acid sequence of SEQ ID NO: 2, or the amino acid sequence of SEQ ID NO: 2 with one or more amino acid substitutions, deletions or insertions; and/or
(c) a CDR-H3 having the amino acid sequence of SEQ ID NO: 3, or the amino acid sequence of SEQ ID NO: 3 with one or more amino acid substitutions, deletions or insertions; and/or
(d) a CDR-L1 having the amino acid sequence of SEQ ID NO: 4, or the sequences of SEQ ID NO: 4, with one or more amino acid substitutions, deletions or insertions; and/or
(e) a CDR-L2 having the amino acid sequence of SEQ ID NO: 5, or the sequences of SEQ ID NO: 5, with one or more amino acid substitutions, deletions or insertions; and/or
(f) a CDR-L3 having the amino acid sequence of SEQ ID NO: 6, or the sequences of SEQ ID NO: 6, with one or more amino acid substitutions, deletions or insertions.

In particular, the data in the examples shows antibody molecules according to the present invention interact with the TACE Dis-Cys domain through residues on the outskirts of the $V_H$ domain and with the catalytic domain through select residues in the $V_L$ domain. This in turn means that the antibody molecules preferably comprise CDR-H1, CDR-H3, CDR-L1 and CDR-L3.

As shown in the examples, the antibody molecule of the present invention can tolerate a number of amino acid alterations to the sequences of the CDRs, while retaining the properties of the parent antibody. By way of example, the amino acid sequences of the CDRs of the antibody molecule may each comprise 1, 2, 3, 4, 5, 6, 7, 8, 9 or 10 amino acid substitutions, deletions or insertions as compared to any one of SEQ ID NOs: 1 to 6. As supported by the experiments in the examples, preferably the following amino acid residues in the CDRs are retained, i.e. they are not the subject of any amino acid substitutions, deletions or insertions made:
CDR-H1: SH31 and YH32; and/or
CDR-H2: SH52, SH56 and YH58
CDR-H3: PH98, YH100, TH100B and WH100D
CDR-L1: QL27, SL28, IL29 and YL32
CDR-L2: HL49 and DL50
CDR-L3: SL91, FL92 and IL94
wherein the residues are numbered according to Kabat numbering. As is well known in the art, the CDRs may be present in a range of different antibody types or framework regions, optionally involving one or more further sequence alterations to ensure retention of a useful property of the antibody as disclosed herein.

Each of the VH and VL domains typically comprise three complementarity determining regions (CDRs) responsible for antigen binding, interspersed by framework regions. In an exemplified embodiment, the present invention provides antibody molecules which comprise a VH domain comprising a CDR-H1, CDR-H2 and CDR-H3 having the sequences of SEQ ID NOs 1, 2 and 3, respectively, and/or a VL domain comprising a CDR-L1, CDR-L2 and CDR-L3 having the sequences of SEQ ID NOs 4, 5 and 6, respectively.

Preferably, the antibody molecules comprise a VH domain having at least 80%, more preferably at least 90%, and still more preferably at least 95% amino acid sequence identity to the amino acid sequence of SEQ ID NO: 7 and/or a VL domain having at least 80%, more preferably at least 90%, and still more preferably at least 95% amino acid sequence identity to having the amino acid sequence of SEQ ID NO: 9.

The present invention also provides an antibody molecule in an IgG format that comprises an amino acid sequences for a heavy chain as set out from amino acid 20 onwards in SEQ ID NO: 15 and a light chain as set out from amino acid 21 onwards in SEQ ID NO 16.

The present invention also provides an antibody molecule in a Fab format that comprises an amino acid sequences for a heavy chain as set out in SEQ ID No: 11 and a light chain as set in SEQ ID NO 12.

Generally, the present invention relates to antibody molecules that are capable of inhibiting a biological activity of TACE, i.e. antagonist antibody molecules as understood by those skilled in the art. By way of example, this includes antibody molecules that are capable of inhibiting the activity of TACE in cleaving a substrate, either a naturally occurring substrate, for example a substrate present on the surface of a cell, or a synthetic substrate in an in vitro cleavage assay, such as the fluorogenic substrate methoxycoumarinyl acetyl-Lys-Pro-Leu-Gly-Leu-dinitrophenyl diaminopropionyl-Ala-Arg-$NH_2$. In a typical experiment, TACE or a biologically active fragment thereof is contacted with the substrate under condition where substrate cleavage may occur. Antibody molecules may then be added to determine whether they are capable of inhibiting the cleavage of the substrate by TACE. Exemplary conditions for carrying out an in vitro assay are provided in the examples below. A cell-based shedding assay is described in experimental examples below and uses the assay described in Willems et al (2010).

As regards the level of TACE inhibition, it is also possible to quantify this using the assays described above. By way of example, TACE inhibition by an antibody molecule of the present invention may be compared to known TACE inhibitors, such as the protein N-TIMP-3 (accession number AAB34532), e.g. full length or mature N-TIMP-3. Preferably, the antibody molecules of the present invention are at least 2-fold, and more preferably at least 5-fold more potent inhibitors of TACE than N-TIMP-3 under identical assay conditions.

Additionally or alternatively, the antibody molecules of the present invention may have one or more further properties, for example which improve the affinity or specificity of their interaction with TACE. For example, the mature ADAM ectodomain contains a globular metalloprotease catalytic domain, a disulphide-dependent disintegrin-cysteine rich (Dis-Cys) domain, and in some cases, an epidermal growth factor (EGF)-like domain (FIG. 6(A)). Although most ADAM catalytic domains appear to share homologous structural topology, significant sequence variation is common throughout the non-catalytic Dis-Cys domains (especially in the "hyper-variable" region (HVR) (13)). Accordingly, it is preferred that the antibody molecules of the present invention have an affinity preference for the complete TACE ectodomain (i.e. the catalytic domain and the Dis-Cys domain) over the isolated catalytic domain, thereby helping to avoid cross-reaction with related ADAM family proteins with similar catalytic domains. Preferably, the affinity preference is at least a 2-fold, more preferably at least a 5-fold and most preferably at least a 10-fold affinity preference for the complete ectodomain over the isolated catalytic domain. The affinity preference of the antibody molecules may be determined in competition experiments well known to those skilled in the art.

Binding kinetics and affinity (expressed as the equilibrium dissociation constant Kd) of the anti-TACE antibody molecules may be determined using standard techniques, such as surface plasmon resonance e.g. using BIAcore analysis.

An anti-TACE antibody molecules may have a dissociation constant for TACE of less than 50 nM, less than 40 nM, less than 30 nM, less than 20 nM, less than 10 nM, or less than 1 nM. For example, an antibody molecule may have an affinity for TACE of 1 to 20 nM, e.g. 9 to 15 nM. Preferably antibody molecules of the present invention have affinity constants ($K_D$) of less than 10 nM, more preferably less than 5 nM and most preferably less than 2 nM. The affinity constants for binding to TACE, or the TACE ectodomain and/or TACE catalytic domain can be determined using techniques well known in the art such as Biacore SPR analysis as exemplified in the experimental examples below.

Anti-TACE antibody molecules may include any polypeptide or protein comprising an antibody antigen-binding site, including Fab, Fab2, Fab3, scFvs, diabodies, triabodies, tetrabodies, minibodies and single-domain antibodies, as well as whole antibodies of any isotype or sub-class. Antibody molecules and methods for their construction and use are described, in for example Holliger & Hudson, Nature Biotechnology 23(9): 1126-1136 (2005).

In some preferred embodiments, the anti-TACE antibody molecule may be a whole antibody. For example an IgG, IgA, IgE or IgM or any of the isotype sub-classes, particularly IgG1 and IgG4. The anti-TACE antibody molecules may be monoclonal antibodies. Anti-TACE antibody molecules may be chimeric, humanised or human antibodies.

Anti-TACE antibody molecules as described herein may be isolated, in the sense of being free from contaminants, such as antibodies able to bind other polypeptides and/or serum components. Monoclonal antibodies are preferred for most purposes, though polyclonal antibodies may also be employed.

Methods of producing anti-TACE antibody molecules include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces. The library may be naive, that is constructed from sequences obtained from an organism which has not been immunised with any of the proteins (or fragments), or may be one constructed using sequences obtained from an organism which has been exposed to the antigen of interest.

In the present invention, the method described in the examples may be employed to screen for further examples of anti-TACE antibodies having antagonistic properties. After production and/or isolation, the biological activity of an anti-TACE antibody molecule may be tested. For example, the ability of the antibody molecule to inhibit the cleavage of a TACE substrate may be determined.

Antibody molecules normally comprise an antigen binding domain comprising an immunoglobulin heavy chain variable domain (VH) and an immunoglobulin light chain variable domain (VL), although antigen binding domains comprising only a heavy chain variable domain (VH) are also possible (e.g. camelid or shark antibodies). Such antibodies are included within the scope of the present invention.

Competition between antibody molecules may be assayed easily in vitro, for example using ELISA and/or by tagging a specific reporter molecule to one antibody molecule which can be detected in the presence of one or more other untagged antibody molecules, to enable identification of antibody molecules which bind the same epitope or an overlapping epitope. Such methods are readily known to one of ordinary skill in the art.

Derivatising Antibody Molecules

The antibody molecules of the present invention may also be derivatised to modify their properties, and in particular their pharmacological properties. An example is the conjugation of antibody molecules to poly(alkylene glycol) molecules, in particular polyethylene glycol (PEG) molecules, that may be used to enhance the half life or other pharmacological properties of polypeptide therapeutics. Pegylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation Pegylation works by increasing the molecular weight of the therapeutic polypeptide by conjugating the polypeptide to one or more PEG polymer molecules. This is particularly applicable to types of antibody molecules that are fragments of complete antibodies such as Fab fragments.

This may be carried out to the antibody molecules of the present invention by reacting suitable functional groups present in the antibody molecules with a reactive poly(alkylene glycol) molecules. Depending on the functional groups available in the antibody molecules of the present invention, it may be possible to pegylate the antibody molecules in a selective way, for example by identifying suitable reactive cysteine residues in the antibody molecules. Poly(alkylene glycol) molecules are interchangeably referred to in the art as poly(alkylene oxide) molecules and are polyethers. Poly (alkylene glycol) molecules may have linear, branched, comb or star structures and generally are highly water soluble. In addition, the basic poly(alkylene glycol) structure may be provided with one or more reactive functional groups such as hydroxy, amine, carboxylic acid, alkyl halide or thiol groups to facilitate the reaction of the poly(alkylene glycol) molecule with other species such as polypeptides. Preferred poly(alkylene glycol) molecules include those substituted at one or more hydroxyl positions with a chemical group, such as an alkyl group having between one and four carbon atoms. Preferred poly(alkylene glycol) molecules for use in accordance with the present invention are polyethylene glycol ("PEG") molecules, although the skilled person would be able to derivatise antibody molecules of the present invention using other poly(alkylene glycol) molecules, such as polypropylene glycol or polyethylene-polypropylene glycol copolymers. Poly (alkylene glycol) molecules, including PEGs, typically have molecular weights between about 400 Da and about 80 kDa, more preferably between about 1 kDa and about 60 kDa, and more preferably between about 5 kDa and about 50 kDa, e.g. molecular weights of 10 kDa, 20 kDa, 30 kDa or 40 kDa. Poly(alkylene glycol) molecules that may be used in accordance with the present invention are well known in the art and publicly available, for example from commercially available sources such as SigmaAldrich.

Imaging Applications

The antibody molecules of the present invention may additionally be labelled to enable them to be employed for imaging, either in conjunction with or independent of their therapeutic uses. Techniques for labelling antibodies are well known in the art that enable the antibodies to be used in a range of imaging and spectroscopic applications. This might be useful in a number of different medical or research applications, for example in the fields of oncology, cardiovascular medicine or graft rejection.

One particular example of the use of the antibody molecules for imaging involves the use of radionuclide labels in nuclear medicine imaging techniques, such as Single Photon Emission Computed Tomography (SPECT), an imaging technique that detects gamma rays emitted from a radionuclide to produce a two dimensional image of the distribution of the radionuclide in a sample or subject, and Positron Emission Tomography (PET), an imaging technique that three-dimensional images by detecting pairs of gamma rays emitted indirectly by a positron-emitting radionuclide introduced into a sample or subject. Antibody molecules having radionuclide labels may also be employed for multi-modal studies in which imaging techniques are combined, either by selecting radionuclides that are active in more than one imaging technique or by labelling the antibody molecules with more than one type of label.

The antibody molecules of the present invention may be labelled with a radionuclide, for example a radionuclide provided as a complex, or conjugated to a second molecule, such as a linker, that is can be associated with the label. Examples of radionuclides for use in imaging techniques or therapy include technetium, rhenium, copper, cobalt, gallium and indium isotopes such as Tc-99m, Re-186, Re-188, Co-57, Ga-67, In-111 (SPECT), Cu-64, Cu-60, Cu-61, Cu-62, Cu-67, Tc-94m, Ga-68, Co-55 (PET). In general, technetium isotopes are employed for imaging purposes, rhenium isotopes for therapeutic purposes and copper isotopes for both imaging and therapy.

Medical Uses

TACE has been reported to have a wide range of substrates, including many substrates that have been linked to cancer (see Murphy, 2008, Table 1). Consequently, the therapeutic inhibition of TACE using the antibodies of the present invention may be a useful approach to targeting a range of TACE-mediated conditions and diseases, such as cancer, immune related disorders, or psoriasis. In particular, the antibody molecules of the present invention may be used for the treatment of brain cancer, breast cancer, colon cancer, gastric cancer, kidney cancer, liver cancer, lung cancer, ovarian cancer, pancreatic cancer, prostate cancer or colorectal cancer, or immune related disorders such as rheumatoid arthritis.

In some embodiments, the antibody molecules of the present invention may be administered in conjunction with a chemotherapeutic agent or in conjunction with radiotherapy. Examples of additional chemotherapeutic agents include an EGFR pathway inhibitor, such as an anti-EGFR antibody or an EGFR kinase inhibitor, such as cetuximab, panitumumab, Iressa (gefitinib or (N-(3-chloro-4-fluoro-phenyl)-7-methoxy-6-(3-morpholin-4-ylpropoxy)quinazolin-4-amine), or Tarceva (erlotinib or N-(3-ethynylphenyl)-6,7-bis(2-methoxyethoxy) quinazolin-4-amine), or other agents such as Herceptin™ (trastuzumab). Further examples of chemotherapeutic agents include alkylating agents, such as cisplatin, carboplatin and oxaliplatin, anthracyclines, plant alkaloids such as taxanes and vinca alkaloids, and topoisomerase inhibitors such as irinotecan, topotecan, amsacrine, etoposide, etoposide phosphate and teniposide, or fluorouracil (5FU).

In a further possibility, the antibody molecules of the present invention may be antibody-drug conjugates in which the antibody molecule is linked to a drug or toxin. This may be done to direct the drug or toxin to a target site in a biological system where TACE is present. This approach may entail engineering the antibody molecule to provide a functional group capable of reacting with the drug or toxin, or alternatively providing the antibody molecule with a linker group that is capable of reacting with the drug or toxin. In this aspect of the present invention, the drug may also be a pro-drug for conversion to active drug at a target site in a patient.

See Moss 2008 review (PM18414459) for summary of drug discovery efforts against TACE and substrates/disease linkages.

In majority of studies comparing tumour to normal tissue (oncomine), it is known that TACE is overexpressed. TACE has been reported to be overexpressed in a wide range of cancers, including brain, breast, colon, gastric, kidney, liver, lung, ovarian, pancreatic, prostate cancer and colorectal cancer (Murphy, 2008, Table 2). This means that these conditions may be potentially treatable using the antibody molecules of the present invention. In addition, substrates of TACE have been linked to cancer, and these include HB-EGF, amphiregulin, heregulin, TNFα, TGFα, notch, MICA and MICB. However, is should be noted that the antibody molecules of the present invention may also be useful where TACE is simply expressed at "normal" physiological levels, depending on the role that TACE plays in the occurrence of the condition. Furthermore, the antibody molecules of the present invention may also find therapeutic use by inhibiting TACE function in cells and tissues within the body other than the diseases tissue or cells where TACE activity may lead to release of ligands that then act on the cancer cells. One such example may be stromal cells that are found within tumours, but which themselves are not "cancer" cells.

HB-EGF—(Yotsumoto 2010 PM20499311), The TACE ligand HB-EGF is a target for treating breast cancer and potentially overcoming resistance to Herceptin.

Amphiregulin—Kenny 2007 show downreg of TGFα and AREG in a cancer cell line and that this overcomes the malignant phenotype. Willmarth 2008, PM18437539, review of AREG as a target in breast cancer.

Also links to overexpression of AREG, HB-EGF, TGFα in androgen independent prostate cancer (Torring 2000, PM10769639)

TGFα—Kenny 2007. Also Borrell-Pages 2003 (PM12606576) TACE is required for release of TGFα and release of TGFα is required for activation of EGFR.

Heregulin—Involved in an autocrine loop via Her3 receptor in NSCLC. Release of Heregulin shown to be driven by TACE using RNAi experiments (Zhou 2006, PM16843264)

MICA and MICB—These are ligands for Natural Killer cell receptors such as NKG2D and may be TACE substrates. Loss of these immunostimulatory molecules from the surface of tumour cells as a result of TACE activity may help them evade Natural Killer cell mediated anti-tumour activity (Waldhauer 2008 PM 18676862).

As TACE can control the release of EGF family ligands it has been proposed that TACE inhibition strategies may be useful in combination with inhibitors of the EGFR pathway such as EGFR antibodies (e.g. cetuximab, panitumumab) and EGFR kinase inhibitors (e.g. Iressa, Tarceva).

Merchant 2008 (PM18281553) demonstrated synergy between TACE inhibition and EGFR pathway inhibitors in colon cancer cell line (HCA-7).

RankL (also known as TRANCE) is a further TACE regulated ligand. See PM 10224132 which discloses evidence of the shedding of RANKL being regulated by TACE, PM 20166980 which provides a general review that targeting RANKL may be useful in multiple myeloma, and PM 19714603 which describes a specific example of a therapy against RANKL (denosumab) being tested in multiple myeloma.

Macrophage colony-stimulating-factor (M-CSF) receptor is a further TACE regulated ligand (PM 19762488).

TACE inhibition could also be useful in combination with inhibitors of other ErbB driven tumours. For example it has been reported that TGFα can impede the ability of herceptin (trastuzumab) to downregulate Her2 and inhibition of TACE could reduce TGFα and synergise with herceptin treatments (Valabrega 2005, PM15735715).

In addition, a role for TACE has more recently been described whereby induction of TACE is associated with chemoresistance/radioresistance and TACE inhibition could be of use in combination with chemotherapy and radiotherapy (Kyula 2010 PM20570921).

Regulation of TACE activity may be important in inflammatory diseases such as arthritis where TACE target proteins such as TNFα, L-selectin and the soluble IL6 receptor are closely linked to the disease and inhibition of TACE activity could be therapeutically useful (Moss 2008 review, PM18414459) TACE as a target in RA.

Inhibition of TACE has also been proposed as a therapeutic strategy in treatment of Stroke (Lovering 2005, PM 15857301) and in Diabetes (Serino 2007, PM17646208).

Inhibition of TACE in airway inflammation models is also known as a strategy for treating inflammatory or allergic based diseases such as asthma (Trifilief et al 2002, PM11934805).

Pharmaceutical Compositions

The anti-TACE antibody molecules of the present invention may be comprised in pharmaceutical compositions with a pharmaceutically acceptable excipient.

A pharmaceutically acceptable excipient may be a compound or a combination of compounds entering into a pharmaceutical composition which does not provoke secondary reactions and which allows, for example, facilitation of the administration of the anti-TACE antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-TACE antibody molecule.

In some embodiments, anti-TACE antibody molecules may be provided in a lyophilised form for reconstitution prior to administration. For example, lyophilised antibody molecules may be re-constituted in sterile water and mixed with saline prior to administration to an individual.

Anti-TACE antibody molecules will usually be administered in the form of a pharmaceutical composition, which may comprise at least one component in addition to the antibody molecule. Thus pharmaceutical compositions may comprise, in addition to the anti-TACE antibody molecule, a pharmaceutically acceptable excipient, carrier, buffer, stabilizer or other materials well known to those skilled in the art. Such materials should be non-toxic and should not interfere with the efficacy of the anti-TACE antibody molecule. The precise nature of the carrier or other material will depend on the route of administration, which may be by bolus, infusion, injection or any other suitable route, as discussed below.

For intra-venous administration, e.g. by injection, the pharmaceutical composition comprising the anti-TACE antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-TACE antibody molecule may be administered alone or in combination with other treatments, either simultaneously or sequentially dependent upon the condition to be treated.

An anti-TACE antibody molecule as described herein may be used in a method of treatment of the human or animal body, including prophylactic treatment (e.g. treatment before the onset of a condition in an individual to reduce the risk of the condition occurring in the individual; delay its onset; or reduce its severity after onset). The method of treatment may comprise administering an anti-TACE antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody molecules are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment or invasive procedure. Suitable formulations and routes of administration are described above.

In some preferred embodiments, the therapeutic effect of the anti-TACE antibody molecule may persist for several half-lives, depending on the dose. For example, the therapeutic effect of a single dose of anti-TACE antibody molecule may persist in an individual for 1 month or more, 2 months or more, 3 months or more, 4 months or more, 5 months or more, or 6 months or more.

Material and Methods

Recombinant Human TACE.

Mature recombinant TACE ectodomain ($Arg^{215}$-$Arg^{651}$) was expressed in baculovirus infected sf9 cells and purified as described by Milla et al. (28). The mature catalytic domain of TACE ($Arg^{215}$-$Val^{477}$-GlySer-$His^6$) was prepared using an identical baculovirus system and purified by immobilized metal affinity chromatography (IMAC).

Selection of Inhibitory Anti-TACE Ectodomain Human ScFv Antibodies.

Recombinant human TACE ectodomain ($Arg^{215}Arg^{651}$) was biotinylated at a 1:1 ratio using N-succinimidyl biotin (Invitrogen AL-01), checked for wild-type activity in a quenched fluorescent peptide cleavage assay (see below) and exposed to the human scFv phage-display library of McCafferty (23) in the presence of 50 µM CT1746 (24). Following two rounds of solution-phase selection, the eluted polyclonal scFv population was cloned into pSANG10-3F (29) and transformed into BL21(DE3) RIPL E. coli (Stratagene 230280). Individual scFv clones were isolated from E. coli periplasm and ELISA screened against immobilised recombinant TACE ectodomain in the absence of CT1746. Comprehensive screening details have been outlined previously (19, 23). Following initial screening, 14 individual anti-TACE scFv clones were expressed in 500 mL auto-induction (30) shake flask cultures and periplasmic fractions were purified by IMAC. Purified scFvs were screened for recombinant TACE inhibition in a quenched-fluorescent peptide assay (see below) and for cell surface TACE inhibition in a PMA stimulated HB-EGF-alkaline phosphatase assay (see below).

Quenched Fluorescent Peptide Cleavage Assay.

Recombinant human TACE catalytic domain and TACE ectodomain were diluted to 1 nM in 50 mM Tris-HCl, 10 mM $CaCl_2$, 0.05% Brij35, 1% DMSO, pH 7.4 and pre-incubated with titrated concentrations of inhibitor for 4-hours at room temperature. Following incubation, each reaction was separated into 200 µL technical quadruplets in a 96-well black Microwell plate (Nunc 237105), and the fluorogenic substrate methoxycoumarinyl acetyl-Lys-Pro-Leu-Gly-Leu-dinitrophenyl diaminopropionyl-Ala-Arg-$NH_2$ (Peptides International SMO-3670-PI) was added to each well (final concentration 1 µM). Every 30 seconds fluorescence was excited at 320 nm and emission recorded at 405 nm in a Tecan Infinite-200 (at 37° C. for 2000 seconds). Individual readings were normalised against a substrate only control and compiled to produce a mean trend for each variable. A linear regression slope for each reaction was calculated in GraphPad Prism ($\Delta FU\ sec^{-1}$) and proteolytic activity was expressed as the slope percentage of an untreated control (% $\Delta FU\ sec^{-1}$). Final results represent mean values from three separate experiments.

ScFv D1 $V_L$-Exchange.

The $V_H$ domain of TACE inhibitory scFv D1 was cloned into a naive human light-chain (λ and κ) phage display library developed by McCafferty and random colonies from the resulting library (hereafter the D1-$V_H$-neo-$V_L$ library) were PCR screened to assess Vs-insert ratio (86% full scFv). Titrated concentrations (0.01 nM, 0.1 nM, 1 nM and 10 nM) of 1:1 biotinylated TACE ectodomain (no CT1746) were exposed to the D1-$V_H$-neo-$V_L$ library for two rounds of solution-phase selection. In addition, identically titrated selections were performed against biotinylated TACE ectodomain immobilised on streptavidin coated Immuno-Tubes (Nunc 444202) (solid-phase selections). Following two rounds of both selections, the eluted polyclonal scFv populations were individually cloned into pSANG10$^{-3}$F and transformed into the E. coli BL21(DE3). Over 1,000 individual scFv clones were isolated from E. coli periplasm and ELISA screened against immobilised recombinant TACE. From all 10 selections, the top 24 clones were individually expressed in 50 mL auto-induction shake flask cultures and periplasmic fractions were purified by IMAC (Satorius VS-MCMINI24). Titrated concentrations of all matured scFvs (including the original D1 scFv) were ELISA screened against 100 nM TACE ectodomain and catalytic domain to identify dual binders.

Paratope Alanine Scanning Mutagenesis.

D1(A12) paratope residues were identified by homology modelling (26) and individual alanine mutants were created using site-directed mutagenesis (Stratagene 200521). Purified recombinant scFvs were subjected to an 8-point fluorometric titration ([TACE]=1 nM) (as above) and a 16-point titration ELISA ([TACE]-500 nM). $IC_{50}$ and $EC_{50}$ values for both D1(A12) (WT) and each alanine mutant (Ala) were calculated using GraphPad Prism. Change in Gibb's Free Energy ($\Delta\Delta G$) was calculated using the equation: $\Delta\Delta G = + RT\ln(Ala/WT)$.

Expression of Recombinant D1(A12) Human FAb.

The $V_H$ and $V_L$ domains of D1(A12) were cloned into a novel human FAb expression vector based on pET22b(+) (upstream of human $C_H1$ and $C_L$-κ respectively). Transformed BL21(DE3) RIPL E. coli were cultured to $OD_{600}$>40 in a 5 L bench-top fermentor, induced with 10 mM IPTG and harvested after a further 4 hours. The periplasmic fraction was isolated by osmotic shock and human FAb was purified by Protein-G affinity chromatography (GE 17-0404-01).

Surface Plasmon Resonance (SPR).

Immobilising TACE on a Biacore SPR chip using amine, aldehyde or biotin coupling rapidly denatures the protein (only linear epitopes accessible). This may explain why there are no reported SPR experiments using TACE. To circumvent this issue, either monovalent D1(A12) FAb or N-TIMP-3 were amine-coupled to a CM5 chip (GE Healthcare) (~200 response units (RU)) and titrated concentrations of TACE were injected. Results represent the mean values of blank-subtracted technical triplicates per concentration variable. All experiments were performed on a Biacore T100 (GE Healthcare) at 37° C. with a flow-rate of 40 L/sec. Binding constants were calculated using Biacore T100 Evaluation Software (1:1 binding model; Rmax <200 RU; tc >1×10$^8$; Chi$^2$<0.5 RU$^2$.

Expression of Recombinant D1(A12) Human IgG1.

The $V_H$ and $V_L$ domains of D1(A12) were cloned into a novel pBudCE4.1 (Invitrogen V532-20) human IgG1 expression vector (κ-variant) and transfected into HEK-293 cells using Fugene 6 (Roche 11988387001). Stably transfected HEK-293 populations were grown to maximum confluence in 10-layer HYPERFlasks (Corning 10030) and human IgG1 was purified from the conditioned media by Protein-L affinity chromatography (Pierce 89929). Traces of bovine serum proteins were removed using Melon Gel technology (Pierce 45206) and the final D1(A12) human IgG1 was buffer exchanged into sterile PBS.

TNF-αCleavage Assay.

Recombinant human TACE was combined with titrated concentrations of D1(A12) FAb (diluted in 50 mM Tris-HCl, 10 mM CaCl$_2$, 0.05% Brij35, 1% DMSO, pH 7.4) and immediately added to 5 μM GST-TNF-α(31). Each reaction was incubated at 37° C., resolved by 12% SDS-PAGE, coomassie stained and individual bands were quantified by densitometry (ImageQuant TL (GE Healthcare)).

TACE Cell Surface Shedding Assays.

For all shedding assays, 4×10$^4$ cells/well (in 300 μL media) were plated in 48-well plate for 36 hours, washed three-times with serum free media and pre-incubated with either D1(A12) Human IgG1, N-TIMP-3 or control Human Plasma IgG (R&D Systems 1-001-A) (diluted in serum free media) for 1 hour. Each well was stimulated with 100 g/mL phorbol 12-myristate 13-acetate (PMA) for and supernatants were harvested after 1 hour. Soluble TNF-α, TGF-α and Amphiregulin were quantified by sandwich ELISA (R&D System Duoset) and HB-EGF alkaline phosphatase was measured as described in Willems et al (2010).

Results

Isolation of An Anti-TACE Ectodomain Inhibitory Human Antibody.

Whilst most TACE drug discovery projects focus on inhibiting the proteolytic capacity of the isolated catalytic domain, the present inventors purposefully chose to antagonise the complete ectodomain (i.e. the catalytic domain and the Dis-Cys domain). In light of both recent structural advances and prior biochemical observations, the inventors hypothesised that selectively targeting non-catalytic regions of the complete TACE ectodomain would produce a more specific cell surface inhibitor. To this end, recombinant human TACE ectodomain was biotinylated, checked for wild-type activity, and exposed to a naïve human scFv antibody phage-display library (23) for two rounds of solution-phase selections. As previous attempts to directly target metalloprotease catalytic sites have resulted in unwanted cross-reactivity (e.g. TIMPs, Pro-Domains and SMIs), we blocked the TACE catalytic cleft with the broad-spectrum metalloprotease inhibitor CT1746 (24) during initial selections (FIG. 1(B)). The resulting TACE ectodomain antigen could therefore not select for antibodies with epitopes dependent on residues deep within the catalytic site. Following ELISA screening (FIG. 7(A)), subsequent positive scFv clones were sequenced to remove replicates, expressed in E. coli and affinity-purified (immobilised metal affinity chromatography (IMAC)) for functional characterisation. Although several inhibitory antibodies were identified by their ability to hinder TACE quenched-fluorescent (QF) peptide proteolysis (FIG. 7(C)), only scFv D1 retained this inhibitory profile when tested against cell surface shedding of HB-EGF (FIG. 7(D)). Comprehensive QF-peptide analysis revealed scFv D1 inhibited TACE ectodomain with similar potency (IC$_{50}$=5.4 (±0.4) nM) to the amino-terminal domain of the natural TACE inhibitor TIMP-3, N-TIMP-3 (IC$_{50}$=3.2 (±0.2) nM) (FIG. 2(A)). However, unlike N-TIMP-3, scFv D1 did not bind the isolated catalytic domain of TACE (FIG. 2(B)). We have previously shown that Protein Disulphide Isomerase (PDI) can alter the three-dimensional topology of the TACE Dis-Cys domain (19). In a similar fashion to the Dis-Cys binding scFv D3, PDI modulation of the TACE ectodomain seriously disrupted scFv D1 immunoreactivity (FIG. 2(C)). When combined with the lack of isolated catalytic domain binding, this observation suggests scFv D1 primarily bound the non-catalytic TACE Dis-Cys domain. Alanine-scanning mutagenesis of individual scFv D1 complementarity determining region (CDR) loops revealed that residues in the variable heavy ($V_H$) chain of scFv D1 were primarily responsible for TACE ectodomain binding. In contrast, the CDR loops of the variable light ($V_L$) chain did not appear to significantly contribute towards the active D1 paratope (FIG. 2(D)). Despite this conservative paratope, scFv D1 appeared to be entirely selective for human TACE (FIG. 8). Collectively, we conclude scFv D1 is a selective $V_H$-dependent inhibitory antibody that primarily binds to the non-catalytic TACE Dis-Cys domain.

Introduction of Catalytic Domain Binding by $V_L$-Exchange.

As scFv D1 bound non-catalytic regions through its $V_H$ domain, yet was close enough to the catalytic site to block small peptide hydrolysis, we concluded that the currently quiescent $V_L$ domain was in close proximity to the TACE catalytic domain. Moreover, we further hypothesised that the non-functional D1 $V_L$-CDRs could be engineered to introduce TACE catalytic domain binding. To explore this idea, the D1-$V_H$ domain was cloned into a naïve human $V_L$ phage-display library and the resulting "D1-$V_H$-neo-$V_L$ library" was stringently re-selected against titrated concentrations of biotinylated TACE ectodomain. As the D1-$V_H$ was already entirely TACE selective through Dis-Cys binding (FIG. 8), we removed CT1746 from all D1-$V_H$-neo-$V_L$ selections to provide neo-$V_L$ domains with uninterrupted access to the TACE catalytic site. The resulting selection scenario encouraged all D1-$V_H$-neo-$V_L$ scFvs to maintain TACE selectivity (by binding to ectodomain Dis-Cys regions through the D1-$V_H$), whilst simultaneously exposing neo-$V_L$ domains to a previously inaccessible catalytic cleft epitope (due to the absence of the small molecule antagonist) (FIG. 1(B)).

Figure 3:
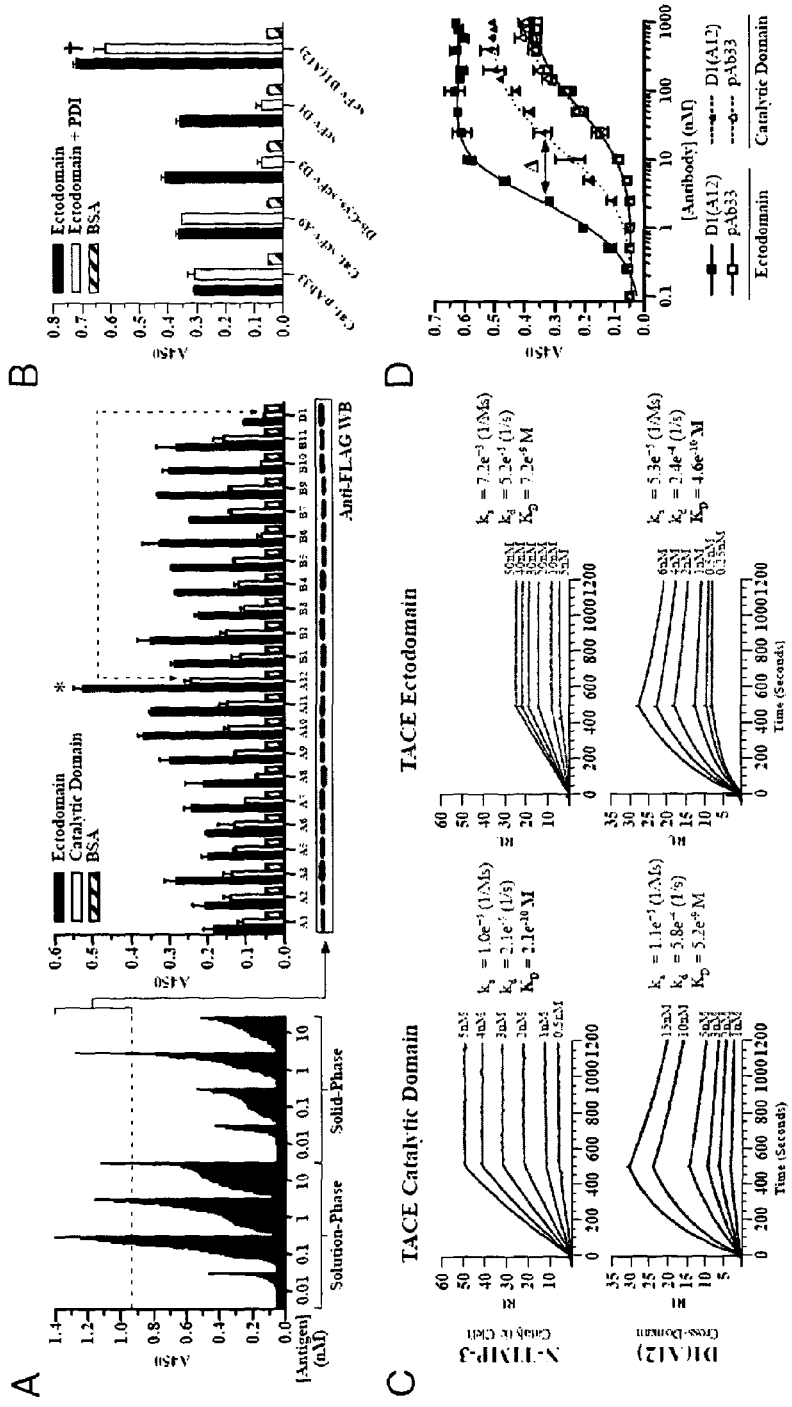
FIG. 3. Introduction of TACE catalytic domain binding by $V_L$-exchange. (A) The $V_H$-domain of scFv D1 was cloned into a naïve human $V_L$ phage-display library and re-selected against titrated concentrations of biotinylated TACE ectodomain in the absence of CT1746 (both solution and solid-phase selections). Selected scFvs were cloned into a FLAG-tagged expression vector and screened for TACE ectodomain binding. The top 30 clones were sequenced to remove replicates (21 remained), individually expressed, affinity-purified and quantitatively re-screened [10 nM] for both TACE ectodomain and catalytic domain binding. For many clones, the neo-$V_L$-domain facilitates independent binding to the TACE catalytic domain. D1-$V_H$-neo-$V_L$ clone "A12" (*) (hereafter D1(A12)) displayed the highest affinity for both antigens. (B) In contrast to scFv D1, scFv D1(A12) is largely resistant to PDI modulation of the TACE Dis-Cys domain (=). This behaviour is similar to antibodies with TACE catalytic domain epitopes. (C) Surface plasmon resonance (SPR) kinetic analysis of N-TIMP-3 (catalytic cleft binding inhibitor) and D1(A12) Fab (cross-domain binding inhibitor) interacting with the isolated TACE catalytic domain and complete ectodomain. Whilst the deep catalytic cleft focus of N-TIMP-3 supports excellent binding to the isolated TACE catalytic domain ($K_D^{Cat}$=211 (±32) pM), binding to the complete ectodomain is seriously disrupted by the additional presence of the non-catalytic TACE Dis-Cys domain ($K_D^{Ecto}$=7,221 (±84) pM) ($\Delta K_D$=$K_D^{Cat}$/

Following two rounds of both solution and solid-phase selections, over 1000 D1-$V_H$-neo-$V_L$ scFvs were re-screened for TACE ectodomain binding. The top 30 clones were isolated, sequenced to remove replicates, individually expressed in E. coli and affinity-purified. D1-$V_H$-neo-$V_L$ lead scFvs were then ELISA screened for their capacity to bind both the complete TACE ectodomain and the isolated catalytic domain (FIG. 3(A)). As predicted, stringent selection of neo-$V_L$ chains against TACE in the absence of CT1746 produced multiple D1-$V_H$-neo-$V_L$ scFv variants now capable of independently binding the isolated TACE catalytic domain and the complete ectodomain. Lead scFv "A12" (hereafter D1(A12)) possessed the highest affinity for both antigens and was advanced for further analysis.

Kinetic Characterisation of the D1(A12)—TACE Interaction.

Screening ELISAs previously implied that the D1-$V_H$-neo-$V_L$ clone D1(A12) could independently bind both the complete TACE ectodomain and the isolated catalytic domain. In addition, D1(A12) is largely resistant to PDI-modulation of the TACE Dis-Cys domain when compared to the parental scFv D1 (FIG. 3(B)). Collectively, these results suggest the D1(A12) epitope contains residues from both the TACE catalytic and Dis-Cys domains. To characterise the kinetics of both interactions, D1(A12) was reformatted to a monovalent human FAb, amine-coupled to a CM5 Biacore chip and titrated concentrations of either the TACE ectodomain or isolated catalytic domain were injected. Surface plasmon resonance (SPR) revealed D1(A12) possessed an affinity constant ($K_D$) of 461 (±65) pM for the complete TACE ectodomain, but only 5,210 (±102) pM for the isolated catalytic domain ($\Delta K_D = K_D^{Cat}/K_D^{Ecto} = 11.3$) (FIG. 3(C)). Whilst the deep catalytic cleft focus of N-TIMP-3 supports excellent binding to the isolated TACE catalytic domain ($K_D^{Cat} = 211$ (±32) pM), binding to the complete ectodomain is seriously disrupted by the additional presence of the non-catalytic TACE Dis-Cys domain ($K_D^{ECto} = 7,221$ (±84) pM) ($DK_D = K_D^{Cat}/K_D^{ECto} = 0.03$). A comparable >10-fold $EC_{50}$ divergence was also observed by inverted titration ELISAs (FIG. 3(D)) ($\Delta EC_{50} = EC_{50}^{Cat}/EC_{50}^{Ecto} = 12.1$). D1(A12) is therefore the first ADAM inhibitor to show an affinity preference for the complete ectodomain over the isolated catalytic domain. This difference in affinity correlates with the multi-domain nature of the D1(A12) epitope generated by "two-step" phage-display selections.

D1(A12) Paratope Scanning Mutageneis.

D1(A12) is an inhibitory TACE human antibody with a >10-fold affinity preference for the complete ectodomain over the isolated catalytic domain. As the initial D1 scFv did not react with the TACE catalytic domain—yet catalytic domain binding was effectively introduced through $V_L$-exchange, we hypothesised that residues within the original D1-$V_H$ interacted with the TACE Dis-Cys and residues within the neo-A12-$V_L$ interacted with the catalytic domain. To comprehensively characterise the D1(A12) paratope, all residues extending beyond the β-carbon were individually mutated to alanine (n=30), expressed in *E. coli* and affinity-purified. The solution-phase QF-peptide $IC_{50}$ of each mutant ($IC_{50}^{Ala}$) was calculated for both the complete TACE ectodomain ($IC_{50}^{Ecto}$) and the isolated catalytic domain ($IC_{50}^{Cat}$) (n=60). In addition, the "wild-type" D1(A12) scFv $IC_{50}$ ($IC_{50}^{WT}$) was simultaneously calculated for both the TACE ectodomain ($IC_{50}^{Ecto} = 0.89$ (±0.04) nM) and catalytic domain ($IC_{50}^{Cat:WT} = 2.3$ (±0.09) nM) using an identical procedure.

Subsequent changes in Gibb's free energy (MAG) were calculated ($\Delta \Delta G = +RT \ln (IC_{50}^{Ala}/IC_{50}^{WT})$) for each mutant and antigen (FIG. 4(A)). In agreement with CDR mutagenesis of scFv D1 (FIG. 2(D)), many D1(A12) $V_H$ residues contribute to $IC_{50}^{Ecto:WT}$. Interestingly, CDR-H1 residues SH31 and YH32, and CDR-H2 residue SH52 (Kabat numbering) appear to exclusively contribute to $IC_{50}^{Ecto:WT}$ and are almost entirely dispensable for achieving $IC_{50}^{Cat:WT}$. Conversely, CDR-L1 residues QL27, SL28 and IL29, and CDR-L3 residues SL91 and FL92 only appear to contribute to $IC_{50}^{Ecto:WT}$ and are almost entirely dispensable for achieving $IC_{50}^{ECto:WT}$. To compliment this solution-phase analysis, solid-phase ELISA $EC_{50}$ $\Delta\Delta G$ values were also calculated for all paratope mutants (FIG. 4(B)). Despite their disparate methodology, the solution and solid-phase D1(A12) paratope $\Delta\Delta G$ profiles are remarkably similar (ectodomain correlation=0.86±0.05; $R^2$=0.91) (catalytic domain correlation=0.82±0.06; $R^2$=0.86). This agreement suggests D1(A12) binding is a direct proxy for TACE inhibition. Importantly, $V_H$ residues SH31, YH32, and SH52 reprised their ectodomain-bias behaviour and $V_L$ residues QL27, SL28, IL29, SL91 and FL92 continue to contribute towards isolated catalytic domain binding.

When mapped onto D1(A12) Fv Rosetta Antibody models (26), residues displaying either antigen bias cluster at polar ends of the paratope. In addition, CDR-H3 represents a dually important intermediate region within the core of the paratope. Collectively, these data strongly suggest that D1(A12) exclusively interacts with TACE Dis-Cys domain through residues on the outskirts of the $V_H$ domain and exclusively interacts with the catalytic domain through select residues in the $V_L$ domain.

D1(A12) Shares An Epitope With TIMP-3.

It is known that the endogenous metalloprotease inhibitor TIMP-3 docks tightly in the catalytic cleft of the isolated TACE catalytic domain. Unfortunately, TIMP-3 also binds to the catalytic site of many metalloproteases and is therefore of limited use as a targeted therapeutic. As D1(A12) partially binds the TACE catalytic domain, we hypothesised that it might share an overlapping epitope with TIMP-3. To investigate this idea, the TACE ectodomain was immobilised on an immunosorp plate, the surface was blocked, and each well was incubated with titrated concentrations of either monovalent D1(A12) human FAb or control human plasma IgG. Subsequent probing with N-TIMP-3 revealed a D1(A12) FAb dose-dependent disruption of N-TIMP-3 binding to TACE ectodomain (FIG. 9(A)). Similar behaviour was observed by inverting the orientation of D1(A12) and N-TIMP-3 (FIG. 9(B)). Both approaches indicated D1(A12) and N-TIMP-3 disrupted binding at a 1:1 primary probe:TACE ectodomain molar ratio. Despite their substantially different binding kinetics, we conclude that D1(A12) shares at least a partial epitope with the endogenous TACE inhibitor TIMP-3.

D1(A12) Potently Inhibits the Complete TACE Ectodomain.

By exploiting ADAM multi-domain topology using two-step antibody phage-display, we have engineered the first ADAM antagonist that displays a significantly higher affinity for the complete ectodomain compared to the isolated catalytic domain. As the eventual goal of this approach was to develop a superior TACE inhibitor, we characterised the translation of this enhanced ectodomain affinity into inhibitory potential. This is the first report of an antagonistic antibody to TACE that has been described in the art, notwithstanding the fact that the cloning of TACE is disclosed in WO 96/041624.

Monovalent D1(A12) FAb proved capable of inhibiting the proteolysis of a macromolecular GST-TNF-α substrate by both the TACE ectodomain and the isolated catalytic domain (FIG. 5(A)). Correlating with previous affinity data, D1(A12) FAb inhibited TACE ectodomain activity more potently than isolated catalytic domain activity ($IC_{50}^{ECto} = 73.9$ (±3.2) nM; $IC_{50}^{Cat} = 124.7$ (±6.2) nM). Moreover, the D1(A12) FAb retained this potent inhibitory capacity in comprehensive QF-peptide analysis (FIG. 5(B)). D1(A12) FAb inhibited the isolated TACE catalytic domain with similar potency to the natural leading TACE inhibitor N-TIMP-3 ($\Delta IC_{50} = IC_{50}^{Cat:N-TIMP-3}/IC_{50}^{Cat:D1(A12)} = 1.35$). However, when identical assays were performed with the complete TACE ectodomain, D1(A12) proved to be >5-fold better than N-TIMP-3 ($\Delta IC_{50} = IC_{50}^{ECto:N-TIMP-3}/IC_{50}^{Ecto:D1(A12)} = 5.75$).

Figure 5C:
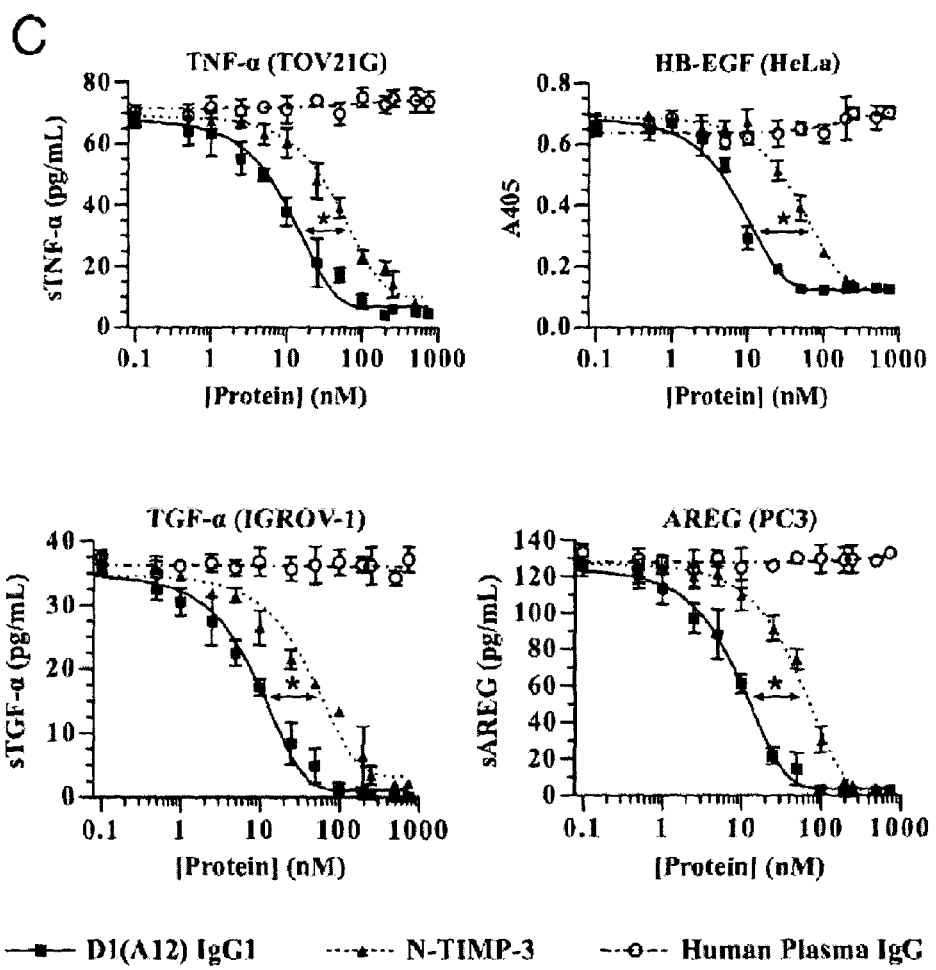

As the rationale for inhibiting the complete TACE ectodomain was to produce a superior cell surface TACE inhibitor, D1(A12) was reformatted to a human IgG1 and compared to N-TIMP-3 in multiple cancer cell-based shedding assays (FIG. 5(C)). The effect of D1(A12) IgG1 on the shedding of four separate TACE ligands was investigated across four human cancer cell lines. Interestingly, the QF-peptide TACE ectodomain inhibitory profiles of D1(A12) and N-TIMP-3 were almost identically repeated in all four cell surface shedding assays. Irrespective of substrate, cell line, or TACE expression levels, D1(A12) human IgG1 routinely inhibited cell surface TACE activity 5-fold better than N-TIMP-3. Similar inhibitory profiles were obtained with the monovalent D1(A12) FAb (FIG. 9)—suggesting only one variable domain per IgG was binding cell surface TACE. ELISA, QF-peptide and cell surface shedding assays also confirm D1(A12) specifically targets TACE and not closely related proteases (FIG. 10). As only the TACE ectodomain is present at the cell surface, this collective data comprehensively demonstrates the antagonistic value in specifically targeting the complete TACE ectodomain.

TABLE S1

D1(A12) $IC_{50}$ data. (A) $IC_{50}$ values from FIG. 9(B). (B) $IC_{50}$ values from FIG. 9. In addition, results from TNFR1α shedding are described. All ± represent SD.

| Inhibitor | Epitope | IC50 (nM) Ectodomain | IC50 (nM) Catalytic Domain | Delta |
|---|---|---|---|---|
| N-TIMP-3 | Catalytic Cleft | 3.1 (±0.15) | 0.6 (±0.02) | 5.2 |
| D1 (A12) FAb | Cross-Domain | 0.45 (±0.01) | 0.54 (±0.02) | 0.8 |

| Substrate | Cell Line | IC50 (nM) D1 (A12) IgG1 | IC50 (nM) N-TIMP-3 | Delta |
|---|---|---|---|---|
| TNF-α | TOV21G | 11.2 (±0.95) | 48.5 (±3.56) | 4.3 |
| TGF-α | IGROV-1 | 9.4 (±2.34) | 44.5 (±4.58) | 4.7 |
| Amphiregulin | PC3 | 9.3 (±1.65) | 53.3 (±1.31) | 5.7 |
| HB-EGF-AP | HeLa | 7.9 (±1.22) | 47.3 (±2.30) | 6.0 |
| TNFR1a | IGROV-1 | 10.4 (±0.97) | 49.5 (±2.51) | 4.7 |
|  | Mean Values: | 9.6 | 48.6 | 5.1 |

Anti-TACE Antibody D1(A12) Sensitizes KrasWT and KrasMT CRC Cells to Chemotherapy Treatment.

Anti-TACE antibody D1(12) was tested to determine the effect when it was used in combination with 5-fluorouracil to sensitize five colorectal cancer (CRC) cell lines to chemotherapy. LoVo, H630, Dks-8, HKH-2, and HCT-116 human CRC cell lines were maintained in DMEM and were treated with indicated concentrations of 5-fluorouracil and of the anti-TACE Ab D1(12). All medium was supplemented with 10% FCS, 50 μg/mL penicillin-streptomycin, 2 mmol/L l-glutamine, and 1 mmol/L sodium pyruvate (Invitrogen). All cells were grown in a humidified atmosphere with 5% $CO_2$ at 37° C. Cell viability was assessed by the tetrazolium dye [3-(4,5-dimethylthiazol-2-yl)-2,5-diphenyltetrazolium bromide, Sigma] assay. Cells were seeded at 2,000 to 4,000 per well in 96-well plates. Cells were treated with increasing doses of 5-fluorouracil for 72 h along with the indicated doses of D1 (A12) antibody. After treatment, cells were washed once with 1×PBS and incubated with medium containing 3-(4,5-dimethylthiazol-2-yl)-2,5-diphenyltetrazolium bromide (0.5 mg/mL) for 3 h at 37° C. Culture medium with 3-(4,5-dimethylthiazol-2-yl)-2,5-diphenyltetrazolium bromide was removed, and formazan crystals were reabsorbed in 200 μL DMSO (Sigma). Cell viability was determined by measuring the absorbance at 570 nm, using a microplate reader (Molecular Devices). $IC_{50}$ was calculated using Prism software package. Each value is representative of at least three independent experiments.

FIG. 16 shows that inhibition of TACE by the anti-TACE antibody of the present invention resulted in synergistic killing of each of the tested colorectal cancer cell lines treated with chemotherapy agents, such as 5-FU. The validates approaches that are based on the combined use of anti-TACE antibodies of the present invention and other chemotherapeutic agents.

Anti-TACE Antibody Abrogates Colorectal Xenograft (H630) Growth In Vivo.

H630 xenografts were established for 14 days prior to once weekly treatment by i.p. administration with control (PBS alone) or the indicated dose of D1(A12) anti-TACE antibody and tumour growth monitored over a period of six weeks. Each group consisted of 8 animals. Female BALB/c severe combined immunodeficient mice were maintained under sterile and controlled environmental conditions (22° C., 50±10% relative humidity, 12-h/12-h light/dark cycle, autoclaved bedding), with food and water ad libitum. Following 14 days of quarantine, mice were included in our protocol. The experiment was carried out in accordance with the Animals (Scientific Procedures) Act, 1986. To determine tumor volume, two axes of the tumors were measured using digital Vernier calipers. Tumor volumes were calculated using the following formula: (longest tumor diameter)×(shortest tumor diameter)$^2$. H630 xenograft mouse models were established by s.c. inoculation of 2×10$^6$ cells into the flanks using Matrigel (BD Biosciences). Tumors were allowed to grow until they reached ~200 mm$^3$ (day 14), at which point the first group received placebo (PBS) and the additional groups received a weekly injection of the indicated dose of the D1(A12) antibody by i.p. administration. Each treatment group contained eight animals. The tumors were measured three times a week in two dimensions using a caliper. The statistical significance was analyzed using the unpaired two-tailed Student's t test.

As shown in FIG. 17, inhibition of TACE by an anti-TACE antibody of the present invention such as D1(12) resulted in inhibition of the growth of a H630 colorectal cancer tumour xenograft. This demonstrates that the antibodies of the present invention are effective in vivo as therapeutic agents.

Plasma Levels of Potential TACE Substrates in a Colorectal Cancer Xenograft.

H630 xenografts were established for 14 days prior to once weekly treatment by i.p. administration with control (PBS alone) or the indicated dose of D1(A12) anti-TACE antibody and tumour growth monitored over a period of six weeks. Each group consisted of 8 animals. Blood plasma was collected post-mortem for analysis of TACE substrate levels. Soluble TNF-α, TGF-α, Amphiregulin and sIL6-R were quantified by sandwich ELISA (R&D System Duoset) and HB-EGF alkaline-phosphatase was measured as described in Willems, et al. (2010).

As shown in FIG. 18, inhibition of TACE by an anti-TACE antibody of the present invention such as D1(12) resulted in reduced levels of a number of TACE substrates in the colorectal H630 cancer tumour xenograft. This demonstrates that the antibody is active in vivo and hence supports it application as a therapeutic agent.

Effect of Anti-TACE Antibody in an IGROV1 Ovarian Cancer Xenograft Model.

We tested the effect of weekly intra-peritoneal dosing in IGROV1-Luc xenografts with 10 mg/kg D1(A12), in comparison with 10 mg/kg infliximab and PBS vehicle. The first dose was given on day 4 and the further doses every 7 days thereafter until the endpoint, which was the point at which the tumour burden approached the maximum permissible. Tumour growth, measured by bioluminescence. Balb/c nude female mice were injected i.p. with 5×10⁶ IGROV1-Luc cells and were observed daily for tumour growth and clinical signs. The endpoint was defined as the point at which the tumour burden began to cause clinical signs such as reduced activity.

Tumour burden was quantified weekly by bioluminescent imaging. Tumour Specific Growth Rate (SGR) for each group was calculated with the following formulae as published: SGR=ln(V2/V1)/T2−t1 where V1 is the initial mean volume on day 4 (t1) prior to treatment, and V2 is the final mean tumour volume at the endpoint (t2). Tumour Doubling Time (DT), in days, =ln(2)/SGR. In an additional analysis of these data, the tumour growth rate for each individual mouse was calculated using the exponential curve fit function in Graphpad PRISM, then the mean k (rate constant) for each group was compared. Significance between treated and vehicle groups was calculated using at Test. Blood plasma was collected post-mortem for analysis of TACE substrate levels. ELISAs for TACE substrates were performed using R&D Systems Duoset kits: human TNF-α(TNFSFIA, cat. No. DY210), human soluble TNFR1-α (TNFRSFIA, cat. No. DY225), human TGF-α (cat. No. DY239), and human Amphiregulin (AREG) (cat. No. DY262). The DY210 kit was confirmed to be specific for human TNF-α by testing recombinant mouse TNF-α with this kit and showing that there was no cross-reactivity.

FIG. 20 shows that inhibition of TACE (by using our D1(12) antibody) also resulted in reduced levels of a number of TACE substrates in the IGROV1 ovarian cancer xenograft model. This demonstrates that the antibody is active in vivo and hence supports it application as a therapeutic agent. The data also shows a reduction in tumour growth in the group treated with our D1(A12) antibody (see FIG. 19).

Pharmacokinetics of Anti-TACE Antibody in Nude Mice.

The pharmacokinetics (PK) of the anti-TACE antibody D1(A12) were investigated using a single 10 mg/kg dose i.p., in non-tumour-bearing mice. FIG. 21 shows the results after a single dose of 10 mg/kg i.p. N=2 or more mice per time point. Error bars represent the standard error of the mean. PK parameters were calculated using the WinNonLin noncompartmental analysis programme: plasma $C_{max}$=523+/−58 nM, Tmax 2 days, half life 8.6 days. This is consistent with published values for half life of human IgG antibodies in mouse plasma.

```
Sequence Listing
SEQ ID NO: 1: CDR-H1 amino acid sequence (from D1(A12))
CAASGFTESSYAMS SEQ ID NO: 2: CDR-H2 amino acid sequence (from D1(A12))
AISGSGGSTYYADSVKG SEQ ID NO: 3: CDR-H3 amino acid sequence (from D1(A12))
CVKDFGPGYGTGWFDY SEQ ID NO: 4: CDR-L1 amino acid sequence (from D1(A12))
CRASQSISSYLN SEQ ID NO: 5: CDR-L2 amino acid sequence (from D1(A12))
IHDASSLQSGV SEQ ID NO: 6: CDR-L3 amino acid sequence (from D1(A12))
CQQSFSIPLTFGG SEQ ID NO: 7: VH domain amino acid sequence (from D1(A12)scFv)
EVQLVESGGGLVRPGGSLRLSCAASGFTFSSYAMSWVRQAPGKGLEWVSAISGSGGSTYYADSVKGRFTISR

DNTKNSLYLQMTSLRADDTAFYYCVKDFGPGYGTGWFDYWGPGTLVTVSA

SEQ ID NO: 8: VH domain nucleic acid sequence (from D1(A12)scFv)
GAAGTGCAGCTGGTGGAGTCTGGGGGAGGCTTGGTACGGCCTGGGGGGTCCCTGAGACTCTCCTGTGCAGCC

TCTGGATTCACCTTTAGCAGCTATGCCATGAGCTGGGTCCGCCAGGCTCCAGGGAAGGGGCTGGAGTGGGTC

TCAGCTATTAGTGGTAGTGGTGGTAGCACATACTACGCAGACTCCGTGAAGGGCCGGTTCACCATCTCCAGA

GACAACACCAAGAACTCCCTGTATCTGCAAATGACGAGTCTGAGAGCTGACGACACGGCCTTTTATTACTGT

GTAAAAGATTTCGGACCCGGTTATGGCACTGGCTGGTTTGACTACTGGGGCCCGGGAACCCTGGTCACCGTC

TCCGCA

SEQ ID NO: 9: VL domain amino acid sequence (from D1(A12)scFv)
SDIQMTQSPSSLSASVGDRVTITCRASQSISSYLNWYQQKPGKAPKLLIHDASSLQSGVPSRFSGSGSGTDF

TLTISSLQPEDFATYYCQQSFSIPLTFGGGTKMDIKR

SEQ ID NO: 10: VL domain nucleic acid sequence (from D1(A12)scFv)
AGCGACATCCAGATGACCCAGTCTCCATCCTCCCTGTCTGCATCTGTAGGAGACAGAGTCACCATCACTTGC

CGGGCAAGTCAGAGCATTAGGAGCTATTTAAATTGGTATCAGCAGAAGCCAGGGAAAGCCCCTAAGCTCCTG

ATCCATGATGCATCCAGTTTGCAAAGTGGGGTCCCATCAAGGTTCAGTGGCAGTGGATCTGGGACAGATTTC

ACTCTCACCATCAGCAGTCTGCAACCTGAAGATTTTGCAACTTACTACTGTCAACAGAGTTTCAGTATTCCC

CTCACTTTCGGCGGAGGGACCAAAATGGATATCAAACGT
```

-continued

SEQ ID NO: 11: D1(A12) amino acid sequence, FAb format, heavy chain
EVQLVESGGGLVRPGGSLRLSCAASGFTFSSYAMSWVRQAPGKGLEWVSAISGSGGSTYYADSVKGRFTISR

DNTKNSLYLQMTSLRADDTAFYYCVKDFGPGYGTGWFDYWGPGTLVTVSAASTKGPSVFPLAPSSKSTSGGT

AALGCLVKDYFPEPVTVSWNSGALTSGVHTFPAVLQSSGLYSLSSVVTVPSSSLGTQTYICNVNHKPSNTKV

DKKVEPKSC

SEQ ID NO: 12: D1(A12) amino acid sequence, FAb format, light chain
SDIQMTQSPSSLSASVGDRVTITCRASQSISSYLNWYQQKPGKAPKLLIHDASSLQSGVPSRFSGSGSGTDF

TLTISSLQPEDFATYYCQQSFSIPLTFGGGTKMDIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTKSFNRGEC

SEQ ID NO: 13: D1(A12) nucleic acid sequence, FAb format, heavy chain
GAAGTGCAGCTGGTGGAGTCTGGGGGAGGCTTGGTACGGCCTGGGGGGTCCCTGAGACTCTCCTGTGCAGCC

TCTGGATTCACCTTTAGCAGCTATGCCATGAGCTGGGTCCGCCAGGCTCCAGGGAAGGGGCTGGAGTGGGTC

TCAGCTATTAGTGGTAGTGGTGGTAGCACATACTACGCAGACTCCGTGAAGGGCCGGTTCACCATCTCCAGA

GACAACACCAAGAACTCCCTGTATCTGCAAATGACGAGTCTGAGAGCTGACGACACGGCCTTTTATTACTGT

GTAAAAGATTTCGGACCCGGTTATGGCACTGGCTGGTTTGACTACTGGGGCCCGGGAACCCTGGTCACCGTC

TCCGCAGCCTCCACCAAGGGCCCATCGGTCTTCCCCCTGGCACCCTCCTCCAAGAGCACCTCTGGGGGCACA

GCGGCCCTGGGCTGCCTGGTCAAGGACTACTTCCCCGAACCGGTGACGGTGTCGTGGAACTCAGGCGCCCTG

ACCAGCGGCGTGCACACCTTCCCGGCTGTCCTACAGTCCTCAGGACTCTACTCCCTCAGGAGCGTGGTGACC

GTGCCCTCCAGGAGCTTGGGCACCCAGACCTACATCTGCAACGTGAATCACAAGCCCAGCAACACCAAGGTG

GACAAGAAAGTTGAGCCCAAATCTTGT
Underlined text = variable domain, Normal text = constant domain.

SEQ ID NO: 14: D1(A12) nucleic acid sequence, FAb format, light chain
AGCGACATCCAGATGACCCAGTCTCCATCCTCCCTGTCTGCATCTGTAGGAGACAGAGTCACCATCACTTGC

CGGGCAAGTCAGAGCATTAGCAGCTATTTAAATTGGTATCAGCAGAAGCCAGGGAAAGCCCCTAAGCTCCTG

ATCCATGATGCATCCAGTTTGCAAAGTGGGGTCCCATCAAGGTTCAGTGGCAGTGGATCTGGGACAGATTTC

ACTCTCACCATCAGCAGTCTGCAACCTGAAGATTTTGCAACTTACTACTGTCAACAGAGTTTCAGTATTCCC

CTCACTTTCGGCGGAGGGACCAAAATGGATATCAAACGTACTGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCAGGAGAGTGTCACAGAGCAGGAC

AGCAAGGACAGCACCTACAGCCTCAGGAGCACCCTGACGCTGAGCAAAGCAGACTACGAGAAACACAAAGTC

TACGCCTGCGAAGTCACCCATCAGGGCCTGAGCTCGCCCGTCACAAAGAGCTTCAACAGGGGAGAGTGT
Underlined text = variable domain, Normal text = constant domain.

SEQ ID NO: 15 and 16: D1(A12) amino acid sequence, IgG1 format, heavy
and light chain
SEQ ID NO: 15 - heavy chain (with leader underlined):
MDWTWRVFCLLAVAPGAHSEVQLVESGGGLVRPGGSLRLSCAASGFTFSSYAMSWVRQAPGKGLEWVSAISG

SGGSTYYADSVKGRFTISRDNTKNSLYLQMTSLRADDTAFYYCVKDFGPGYGTGWFDYWGPGTLVTVSAAST

KGPSVFPLAPSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGK

SEQ ID NO: 16 - light chain (with leader underlined):
MAWTPLWLTLFTLCIGSVVSSDIQMTQSPSSLSASVGDRVTITCRASQSISSYLNWYQQKPGKAPKLLIHDA

SSLQSGVPSRFSGSGSGTDFTLTISSLQPEDFATYYCQQSFSIPLTFGGGTKMDIKRTVAAPSVFIFPPSDE

-continued
QLKSGTASVVCLLNNFYPREAKVQWKVDNALQSGNSQESVTEQDSKDSTYSLSSTLTLSKADYEKHKVYACE

VTHQGLSSPVTKSFNRGEC

SEQ ID NO: 17 and 18: D1(A12) nucleic acid sequence, IgG format.
SEQ ID NO: 17 - heavy chain (with leader underlined):
<u>ATGGACTGGACCTGGAGGGTCTTCTGCTTGCTGGCTGTAGCACCAGGTGCCCACTCC</u>GAAGTGCAGCTGGTG

GAGTCTGGGGGAGGCTTGGTACGGCCTGGGGGGTCCCTGAGACTCTCCTGTGCAGCCTCTGGATTCACCTTT

AGCAGCTATGCCATGAGCTGGGTCCGCCAGGCTCCAGGGAAGGGGCTGGAGTGGGTCTCAGCTATTAGTGGT

AGTGGTGGTAGCACATACTACGCAGACTCCGTGAAGGGCCGGTTCACCATCTCCAGAGACAACACCAAGAAC

TCCCTGTATCTGCAAATGACGAGTCTGAGAGCTGACGACACGGCCTTTTATTACTGTGTAAAAGATTTCGGA

CCCGGTTATGGCACTGGCTGGTTTGACTACTGGGGCCCGGGAACCCTGGTCACCGTCTCCGCAGCCTCCACC

AAGGGCCCATCGGTCTTCCCCCTGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGAAAGTTGAG

CCCAAATCTTGTGACAAAACTCACACATGCCCACCGTGCCCAGCACCTGAACTCCTGGGGGGACCGTCAGTC

TTCCTCTTCCCCCCAAAACCCAAGGACACCCTCATGATCTCCCGGACCCCTGAGGTCACATGCGTGGTGGTG

GACGTGAGCCACGAAGACCCTGAGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCAGCCCCCATCGAGAAAACCATC

TCCAAAGCCAAAGGGCAGCCCCGAGAACCACAGGTGTACACCCTGCCCCCATCCCGGGATGAGCTGACCAAG

AACCAGGTCAGCCTGACCTGCCTGGTCAAAGGCTTCTATCCCAGCGACATCGCCGTGGAGTGGGAGAGCAAT

GGGCAGCCGGAGAACAACTACAAGACCACGCCTCCCGTGCTGGACTCCGACGGCTCCTTCTTCCTCTATAGC

AAGCTCACCGTGGACAAGAGCAGGTGGCAGCAGGGGAACGTCTTCTCATGCTCCGTGATGCATGAGGCTCTG

CACAACCACTACACGCAGAAGAGCCTCTCCCTGTCTCCGGGTAAA

SEQ ID NO: 18 - light chain (with leader underlined):
<u>ATGGCCTGGACCCCTCTCTGGCTCACTCTCTTCACTCTTTGCATAGGTTCTGTGGTTTCT</u>AGCGACATCCAG

ATGACCCAGTCTCCATCCTCCCTGTCTGCATCTGTAGGAGACAGAGTCACCATCACTTGCCGGGCAAGTCAG

AGCATTAGCAGCTATTTAAATTGGTATCAGCAGAAGCCAGGGAAAGCCCCTAAGCTCCTGATCCATGATGCA

TCCAGTTTGCAAAGTGGGGTCCCATCAAGGTTCAGTGGCAGTGGATCTGGGACAGATTTCACTCTCACCATC

AGCAGTCTGCAACCTGAAGATTTTGCAACTTACTACTGTCAACAGAGTTTCAGTATTCCCCTCACTTTCGGC

GGAGGGACCAAAATGGATATCAAACGTACTGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGC

ACCTACAGCCTCAGCAGCACCCTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGAGAGTGT

SEQ ID NO: 19: TACE amino acid sequence.
Signal Sequence - amino acids 1 to 17 (italics)
Pro-Domain - amino acids 18 to 214 (underlined)
Catalytic Domain - amino acids 215 to 477
Dis-Cys - amino acids 478 to 671 (italics)
Transmembrane Domain - amino acids 672-694 (underlined)
Intracellular Domain - amino acids 695 to 824
The TACE fragment (Arg$^{215}$-Arg$^{651}$) used in the experiments in the
examples runs between and including the R residues shown in bold
text in SEQ ID NO: 19.
*MRQSLLFLTSVVPFVLA*<u>PRPPDDPGFGPHQRLEKLDSLLSDYDILSLSNIQQHSVRKRDLQTSTHVETLLTF</u>

<u>SALKRHFKLYLTSSTERFSQNFKVVVVDGKNESEYTVKWQDFFTGHVVGEPDSRVLAHIRDDDVIIRINTDG</u>

-continued

AEYNIEPLWREVNDTKDKRMLVYKSEDIKNVSRLQSPKVCGYLKVDNEELLPKGLVDREPPEELVHRVKRRA

DPDPMKNTCKLLVVADHRFYRYMGREESTTTNYLIELIDRVDDIYRNTSWDNAGFKGYGIQIEQIRILKSP

QEVKPGEKHYNMAKSYPNEEKDAWDVKMLLEQFSFDIAEEASKVCLAHLFTYQDFDMGTLGLAYVGSPRANS

HGGVCPKAYYSPVGKKNIYLNSGLTSTKNYGKTILTKEADLVTTHELGHNFGAEHDPDGLAECAPNEDQGGK

YVMYPIAVSGDHENNKMFSNCSKQSIYKTIESKAQECFQER*SNKVCGNSRVDEGEECDPGIMYLNNDTCCNS*

*DCTLKEGVQCSDRNSPCCKNCQFETAQKKCQEAINATCKGVSYCTGNSSECPPPGNAEDDTVCLOLGKCKDG*

*KCIPFCEREQQLESCACNETDNSCKVCCRDLSGRCVPYVDAEQKNLFLRKGKPCTVGFCDMNGKCEKRVQDV*

*IER*FWDFIDQLSINTFGKFLADN<u>IVGSVLVFSLIFWIPFSILVHC</u>VDKKLDKQYESLSLFHPSNVEMLSSMD

SASVRIIKPFPAPQTPGRLQPAPVIPSAPAAPKLDHQRMDTIQEDPSTDSHMDEDGFEKDPFPNSSTAAKSF

EDLTDHPVTRSEKAASFKLQRQNRVDSKETEC

REFERENCES

All documents mentioned in this specification are incorporated herein by reference in their entirety.

Murphy, Nature Reviews: Cancer, 8(12): 929-941, 2008.
Moss et al., Nature Clinical Practice, 4(6): 300-309, 2008.
WO 96/041624.
Edwards et al., Mol. Aspects Med., 29(5):258-289, 2008.
Willems et al., Biochem. J., 428: 439-450, 2010.
Milla et al., J. Biol. Chem., 274(43):30563-30570, 1999.
Martin et al., BMC Biotechnology 6: 46, 2006.

The invention claimed is:

1. An isolated antibody molecule which specifically binds to TNF-α Converting Enzyme (TACE) and inhibits a biological activity of TACE, wherein said TACE comprises the amino acid sequence of SEQ ID NO: 19, said antibody comprises the CDR sequences of SEQ ID NOs: 1-6 inclusive, and said biological activity is cleavage of a substrate by TACE.

2. The antibody molecule of claim 1, wherein the antibody inhibits a biological activity of TACE by binding to both the catalytic domain and the Dis-Cys domain of TACE.

3. The antibody molecule of claim 1, wherein the antibody molecule is at least a 2-fold more potent inhibitor of TACE than N-TIMP-3 under identical assay conditions.

4. The antibody molecule of claim 1, wherein the antibody molecule has an affinity preference for the complete TACE ectodomain over the isolated catalytic domain of at least a 2-fold.

5. The antibody molecule of claim 1, wherein the antibody molecule is a complete antibody, a Fab fragment, a F(ab')2 fragment, a scFv, a diabody, or a triabody.

6. The antibody molecule of claim 1 wherein the antibody molecule is a human antibody, a humanised antibody, a bispecific antibody or a chimeric antibody.

7. An antibody molecule according to claim 1 which is a whole antibody.

8. A pharmaceutical composition comprising an antibody molecule according to claim 1 and a pharmaceutically acceptable excipient.

* * * * *